United States Patent
Keady et al.

(10) Patent No.: US 8,848,939 B2
(45) Date of Patent: Sep. 30, 2014

(54) METHOD AND DEVICE FOR ACOUSTIC SEALING AND OCCLUSION EFFECT MITIGATION

(75) Inventors: John P. Keady, Fairfax Station, VA (US); Gary Hoshizaki, Fountain Hills, AZ (US)

(73) Assignee: Personics Holdings, LLC., Boca Raton, FL (US)

( * ) Notice: Subject to any disclaimer, the term of this patent is extended or adjusted under 35 U.S.C. 154(b) by 0 days.

(21) Appl. No.: 12/785,682

(22) Filed: May 24, 2010

(65) Prior Publication Data

US 2011/0235843 A1 Sep. 29, 2011

Related U.S. Application Data

(63) Continuation of application No. 12/706,301, filed on Feb. 16, 2010, now abandoned.

(60) Provisional application No. 61/152,545, filed on Feb. 13, 2009, provisional application No. 61/161,241, filed on Mar. 18, 2009.

(51) Int. Cl.
*H04R 25/00* (2006.01)
*A61F 11/10* (2006.01)

(52) U.S. Cl.
CPC ..................................... *A61F 11/10* (2013.01)
USPC ............. 381/72; 381/322; 381/324; 381/328

(58) Field of Classification Search
CPC .. H01R 1/1016; H01R 1/1083; H01R 25/456; H01R 25/652; H01R 2460/15; A61F 11/10
USPC ............. 381/328, 72, 312, 322, 324; 181/135
See application file for complete search history.

(56) References Cited

U.S. PATENT DOCUMENTS

| | | | |
|---|---|---|---|
| 2,535,258 A | 12/1950 | Bland | |
| 2,824,558 A * | 2/1958 | Michael et al. | 128/865 |
| 3,602,654 A | 8/1971 | Victoreen | |
| 4,133,984 A | 1/1979 | Akiyama | |
| 4,741,344 A | 5/1988 | Danby et al. | |
| 4,834,211 A | 5/1989 | Bibby et al. | |
| 4,896,679 A | 1/1990 | St. Pierre | |
| 4,962,537 A | 10/1990 | Basel et al. | |
| 5,333,622 A | 8/1994 | Casali et al. | |
| 5,483,027 A | 1/1996 | Krause | |
| 6,094,494 A | 7/2000 | Haroldson | |

(Continued)

OTHER PUBLICATIONS

Kichol Lee and John G. Casali; Investigation of the Auditory Occlusion Effect with Implications for Hearing Protection and Hearing Aid Design; Proceedings of the Human Factors and Ergonomics Society 55th Annual Meeting—Sep. 2011; pp. 1783-1787.

*Primary Examiner* — Matthew Eason
(74) *Attorney, Agent, or Firm* — Pablo Meles

(57) ABSTRACT

A system to occlude an ear canal is provided. The system includes an expandable device, a reservoir, a channel coupled between the expandable device and the reservoir, and a pump. The pump expands the expandable device such that a surface of the expandable device contacts an ear canal wall and imparts a force onto the ear canal wall, to produce a tensional strain in the ear canal wall. The strained ear canal wall impedes bodily-propagated sound from entering the ear canal through the ear canal wall, to reduce an occlusion effect by the bodily-propagated sound.

21 Claims, 12 Drawing Sheets

(56) References Cited

U.S. PATENT DOCUMENTS

| | | |
|---|---|---|
| 6,256,396 B1 | 7/2001 | Cushman |
| 6,339,648 B1 | 1/2002 | McIntosh et al. |
| 6,393,130 B1 | 5/2002 | Stonikas et al. |
| 6,513,621 B1 * | 2/2003 | Deslauriers et al. .......... 181/130 |
| 6,671,381 B1 | 12/2003 | Lux-Wellenhof |
| 7,130,437 B2 | 10/2006 | Stonikas et al. |
| 7,164,775 B2 | 1/2007 | Meyer et al. |
| 7,227,968 B2 | 6/2007 | van Halteren et al. |
| 7,362,875 B2 | 4/2008 | Saxton et al. |
| 7,387,187 B2 | 6/2008 | Widmer et al. |
| 2003/0165246 A1 * | 9/2003 | Kvaloy et al. ................. 381/312 |
| 2006/0159298 A1 | 7/2006 | von Dombrowski et al. |
| 2007/0116319 A1 | 5/2007 | Hagberg |
| 2008/0144871 A1 | 6/2008 | Purcell et al. |
| 2009/0173353 A1 | 7/2009 | Purcell et al. |
| 2009/0320858 A1 | 12/2009 | Purcell et al. |
| 2009/0320859 A1 | 12/2009 | Purcell et al. |

* cited by examiner

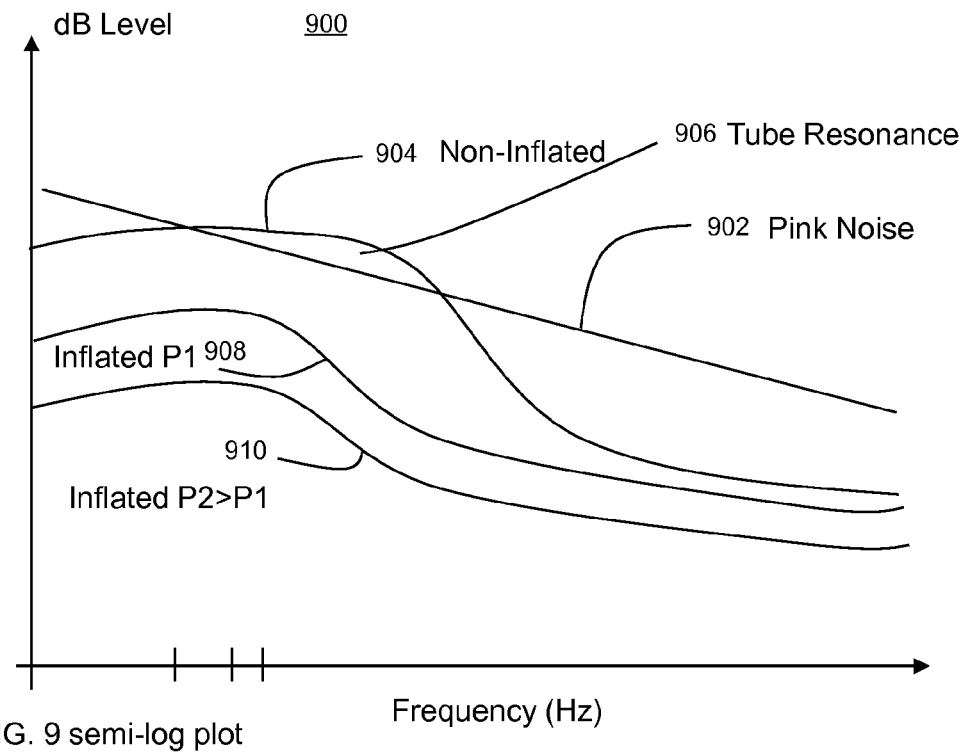
FIG. 9 semi-log plot
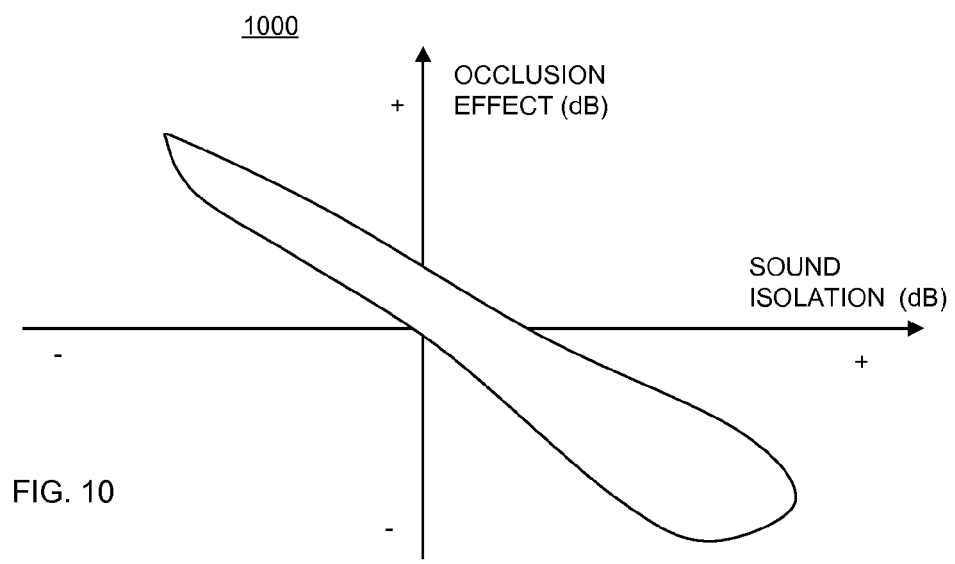
FIG. 10

1500

METHOD AND DEVICE FOR ACOUSTIC SEALING AND OCCLUSION EFFECT MITIGATION

CROSS-REFERENCE TO RELATED APPLICATIONS

This application is a Continuation of patent application Ser. No. 12/706,301 filed 16 Feb. 2010 now abandoned which claims the benefit of U.S. provisional patent application No. 61/152,545 filed on 13 Feb. 2009 and provisional patent application No. 61/161,241 filed 18 Mar. 2009. All disclosures of which are incorporated herein by reference in its entirety.

FIELD OF THE INVENTION

The present invention relates to devices that can be inserted into orifices and more particularly, though not exclusively, a device that can be inserted into body orifices.

BACKGROUND OF THE INVENTION

With the advent of an industrial society, people are exposed to noise pollution at greater and greater levels; both from background, such as street traffic, airplanes, construction sites and intentional exposure to high sound levels such as cell phones, MP3 players, and rock concerts. Studies show that ear damage, leading to permanent hearing impairment is not only increasing in the general population, but increasing at a significantly faster rate in younger populations.

The potential for hearing damage is a function of both the level and the duration of exposure to the sound stimulus. Studies have also indicated that hearing damage is a cumulative phenomenon. Although hearing damage due to industrial or background noise exposure is more thoroughly understood, the risk of exposing one's self to excessive noise, especially with the use of headphones has also been recently studied. Protecting the ear from ambient noise is primarily done with the use of static earplugs that attempt to shield the inner ear from excessively high decibel noise.

Devices have been developed over the years to reduce sound from entering the ear canal. These devices known as earpieces, typically fit into the ear or around the ear. For example, headphones, earbuds, behind the ear earpieces, hearing aids, headsets and other devices attenuate sound from the ambient environment and direct acoustic energy to the tympanic membrane of the ear. People typically do not have knowledge of the cumulative sound levels that they receive on a daily basis. Moreover, both short term and long term noise exposure can be a health risk. Accordingly, a system that overcomes the shortcomings in the related art would be useful.

SUMMARY OF THE INVENTION

A system to occlude an ear canal includes a resilient reservoir and an expandable device. The resilient reservoir has a first volume in a quiescent state and a second volume when the system occludes the ear canal. The resilient reservoir is coupled to an expandable device. Medium in the resilient reservoir is transferred to expand the expandable device to occlude the ear canal. The resilient reservoir is at the second volume when the ear canal is occluded. The resilient reservoir is passively filled with the medium when the expandable device is in an unexpanded state.

A method of returning a resilient reservoir to a first volume of a quiescent state. A permeable membrane is exposed to the medium. The medium diffuses through the membrane. The diffused medium is coupled to the resilient reservoir to provide additional medium to increase the resilient reservoir to the first volume of the quiescent state.

A device for occluding an ear canal comprises a support structure, an expandable device, a variable volume housing, and a resilient reservoir. The expandable device overlies a portion of the support structure. The variable volume housing is coupled to the support structure. The resilient reservoir is within the housing and is coupled to the expandable device. The resilient reservoir provides a medium that expands the expandable device. The resilient reservoir includes a port coupled to the medium when the resilient reservoir is in a quiescent state.

Further areas of applicability of exemplary embodiments of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

Exemplary embodiments of present invention will become more fully understood from the detailed description and the accompanying drawings, wherein:

FIG. 9 is a graph illustrating sound isolation as a function of inflation of an inflatable system in accordance with at least one exemplary embodiment;

FIG. 10 is a graph of sound isolation versus occlusion effect in accordance with at least one exemplary embodiment;

DETAILED DESCRIPTION OF EXEMPLARY EMBODIMENTS OF THE PRESENT INVENTION

Figure 1:
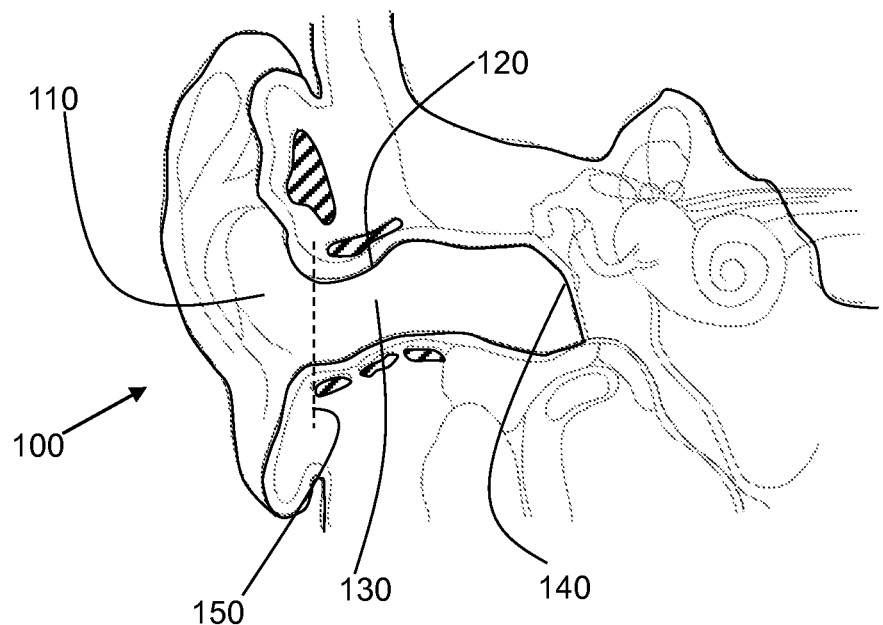
FIG. 1 illustrates general physiology of an ear.

The following description of exemplary embodiment(s) is merely illustrative in nature and is in no way intended to limit the invention, its application, or uses.

Exemplary embodiments are directed to or can be operatively used on various wired or wireless earpieces devices (e.g., earbuds, headphones, ear terminal, behind the ear devices or other acoustic devices as known by one of ordinary skill, and equivalents). For example, the earpieces can be without transducers (for a noise attenuation application) or one or more transducers (e.g. ambient sound microphone (ASM), ear canal microphone (ECM), ear canal receiver (ECR)) for monitoring/providing sound. In all of the examples illustrated and discussed herein, any specific values should be interpreted to be illustrative only and non-limiting. Thus, other examples of the exemplary embodiments could have different values.

Processes, techniques, apparatus, and materials as known by one of ordinary skill in the art may not be discussed in detail but are intended to be part of the enabling description where appropriate. For example specific materials may not be listed for achieving each of the targeted properties discussed, however one of ordinary skill would be able, without undo experimentation, to determine the materials needed given the enabling disclosure herein.

Notice that similar reference numerals and letters refer to similar items in the following figures, and thus once an item is defined in one figure, it may not be discussed or further defined in the following figures. Processes, techniques, apparatus, and materials as known by one of ordinary skill in the relevant art may not be discussed in detail but are intended to be part of the enabling description where appropriate.

FIG. 1 illustrates general physiology of an ear. The ear comprises a pinna 100, concha 110, ear canal wall 120, and tympanic membrane 140. Pinna 100 is an external portion of the ear. Pinna 100 is a cartilaginous region of the ear that focuses acoustic information from an ambient environment to an ear canal 130. Concha 110 is also an external portion of the ear. Concha 110 is a bowl shaped region in proximity to the ear canal opening.

A dashed line 150 indicates an opening to the ear where sound enters to be received by tympanic membrane 140. The ear canal wall 120 forms an acoustic chamber known as ear canal 130. Ear canal shapes and sizes vary substantially over the human population. Ear canal 130 terminates in tympanic membrane 140. Tympanic membrane 140 is a flexible membrane in the middle ear that couples to components of the inner ear. In general, the acoustic information resident in ear canal 130 vibrates tympanic membrane 140 that is converted to a signal (corresponding to the sound) that is provided to the auditory nerve.

Figure 2:
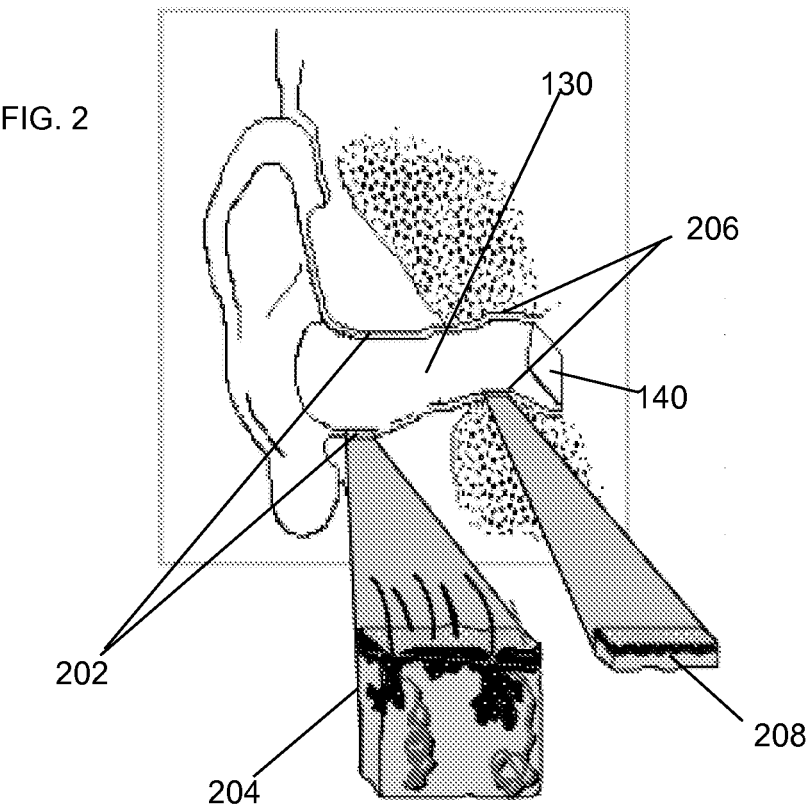
FIG. 2 illustrates a cartilaginous region and a bony region of an ear canal.

FIG. 2 illustrates a cartilaginous region and a bony region of an ear canal 130. The cartilaginous region corresponds to an ear canal wall region 202 and a bony region corresponds ear canal wall region 206 of ear canal wall 120. Ear canal wall region 206 is defined as the area where bone underlies the ear canal wall. As shown, region 206 is located in a second portion of the ear canal near the tympanic membrane 140. The skin layer of ear canal wall 120 in region 206 is sensitive to pressure. The skin layer in region 206 is approximately one tenth the thickness of the skin in ear canal wall region 202. Thus, there is not much tissue separating skin from bone. Placing an object such as an ear plug in this region can stimulate nerves due to skin being pressed against bone which can be uncomfortable and even induce significant pain. Another fact is that region 206 can radiate sound into ear canal 130 as vibrations are conducted through bone and radiated as sound into ear canal 130.

Ear canal wall region 202 is located in a first portion of ear canal 130 closest to the ear opening. Region 202 is a portion of the ear canal wall 120 that includes a layer of cartilage underlying the skin layer. Region 202 is a highly flexible region having no substantial rigid structure. A difference of between regions 202 and 206 is illustrated in an exploded view of tissue 204 and tissue 208. Tissue 204 of region 202 is approximately ten times thicker than tissue 208 of region 206. The cartilage and skin of region 202 is flexible thereby making this region somewhat elastic relative to region 206. Thus, region 202 can be deformed when a force is applied to the area. In general, region 202 is much more insensitive to pressure (comfort/pain) than region 206. It should be noted that applying pressure to ear canal wall 120 such that ear canal wall 120 is deformed stretches and places the skin under tension.

Figure 3:
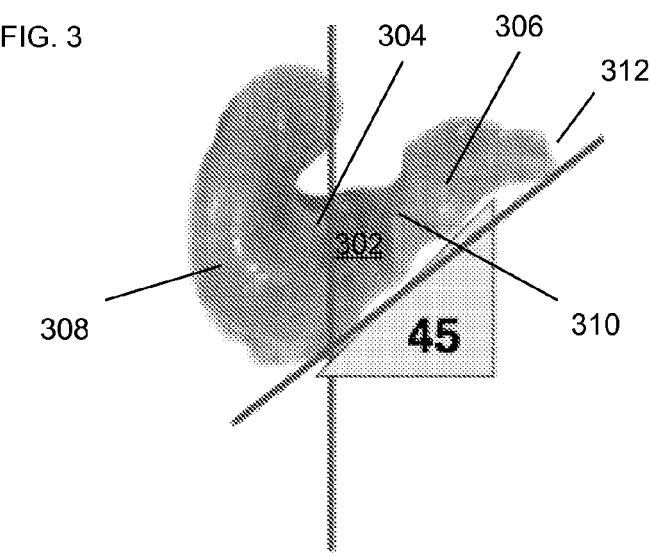
FIG. 3 is an illustration of an ear canal.

FIG. 3 is an illustration of an ear canal 302. The illustration is a mold 310 of an ear canal 302 in an orientation looking towards the face on an individual. The mold 310 also includes concha bowl 308 that is a component of the outer ear adjacent to the ear canal opening. Ear canal 302 has an upward tilt of approximately 45 degrees from the horizontal such that tympanic membrane 312 is above an ear canal opening. In general, an ear canal is not straight or regularly shaped. Ear canal 302 typically has a first bend 304 near the ear canal entrance and a second bend 306 that is proximate to tympanic membrane 312. It should be noted that the volume, shape, and length of ear canal 302 can vary substantially from person to person. Thus, there has been difficulty in providing a system that can effectively seal the ear, attenuate noise, mitigate occlusion effect, works under different environmental conditions, and fits a majority of the population. For example, hearing aid manufacturers have resorted to a full custom earpiece for individuals that include a mold of the patient's ear canal. The ear canal mold is then used to form a hearing aid housing. The procedure to create an ear canal mold is costly, cumbersome, and is not easily adaptable for high volume production.

Figure 4:
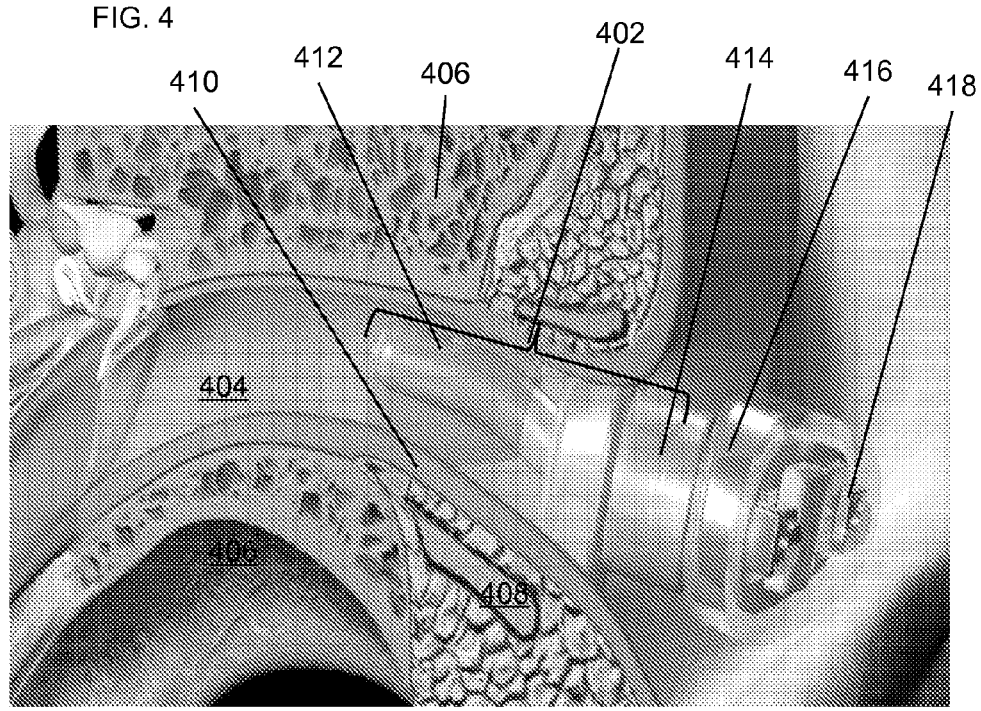
FIG. 4 is an illustration of an earpiece inserted in an ear canal in accordance with at least one exemplary embodiment.

FIG. 4 is an illustration of an earpiece inserted in an ear canal 404 in accordance with at least one exemplary embodiment. The earpiece comprises a sealing section 402 for sealing the ear, a first housing 416, and a second housing 418. Sealing section 402 creates an ear canal volume 404 that is isolated from an ambient environment. Sealing section 402 reduces sound from reaching ear canal volume 404 through two paths. The first path is the opening to the ear canal, which is sealed. The second path for sound to enter ear canal volume 404 is through bone conduction. The second path can provide significant acoustic energy to ear canal volume 404 when the wearer of the earpiece speaks. How sealing section 402 reduces sound from reaching ear canal volume 404 will be discussed in greater detail hereinbelow.

Sealing section 402 comprises a first section 410 and a second section 414. Second section 414 prevents a user of the earpiece from inserting the device too deeply into the ear canal. Second section 414 is designed to be larger than a majority of ear openings but can have a region that fits and seals the ear canal opening.

First section 410 is inserted in the ear canal leaving ear canal volume 404 remaining. The device is designed so that the insertion depth is less than the ear canal length. First section 410 contacts an ear canal wall and seals the ear canal. As shown, first section 410 can contact both a bony region 406 and a cartilaginous region 408 of the ear canal. In at least one exemplary embodiment, a surface of first section 410 in contact with the ear canal wall is under tensile stress. Furthermore, a radial force is applied to first section 410 to hold the surface against the ear canal wall. As shown, first section 410 can be formed on a stent 412 having one or more acoustic channels for providing and receiving sound.

In at least one exemplary embodiment, first housing 416 houses components of the earpiece. For example, first housing 416 can hold an instrument package comprising an ear canal receiver and an ear canal microphone. The ear canal receiver is a speaker that is coupled to an acoustic channel of stent 412 for providing sound to ear canal volume 404. Similarly, the ear canal microphone is coupled to an acoustic channel of stent 412 for receiving sound in ear canal volume 404. Furthermore, first housing 416 can house components for increasing or decreasing a volume of first section 410. For example, the volume of first section 410 is reduced to simplify removal and or insertion of sealing section 402 from the ear canal. Conversely, first section 410 is expanded for sealing the ear canal after an insertion process.

Housing 418 includes further components of the earpiece system. An ambient sound microphone can be placed in housing 418 for receiving sound in the ambient environment. Electronic components for managing audio content, modifying audio content, power management (including a battery), a/d conversion, d/a conversion, mixing, amplification, wired/wireless communication, time, and location can be included in housing 418. In general, isolating ear canal volume 404 from the ambient environment provides an opportunity to monitor sound in the ear canal. By monitoring sound received by the user of the system, an action can be taken to mitigate potential hearing damage should sound levels in the short term or over a longer period of time pose a risk to the user. Isolation from the ambient environment from a hearing perspective can result in reduced situation awareness. For example, people listening to music with earpiece are often not cognizant of potential dangers in the ambient environment that they would normally recognize (e.g. siren or warning).

The electronic components in housing 418 can be used to identify and provide sounds of importance (e.g. siren or warning) to a user when picked up by the ambient sound microphone.

Figure 5:
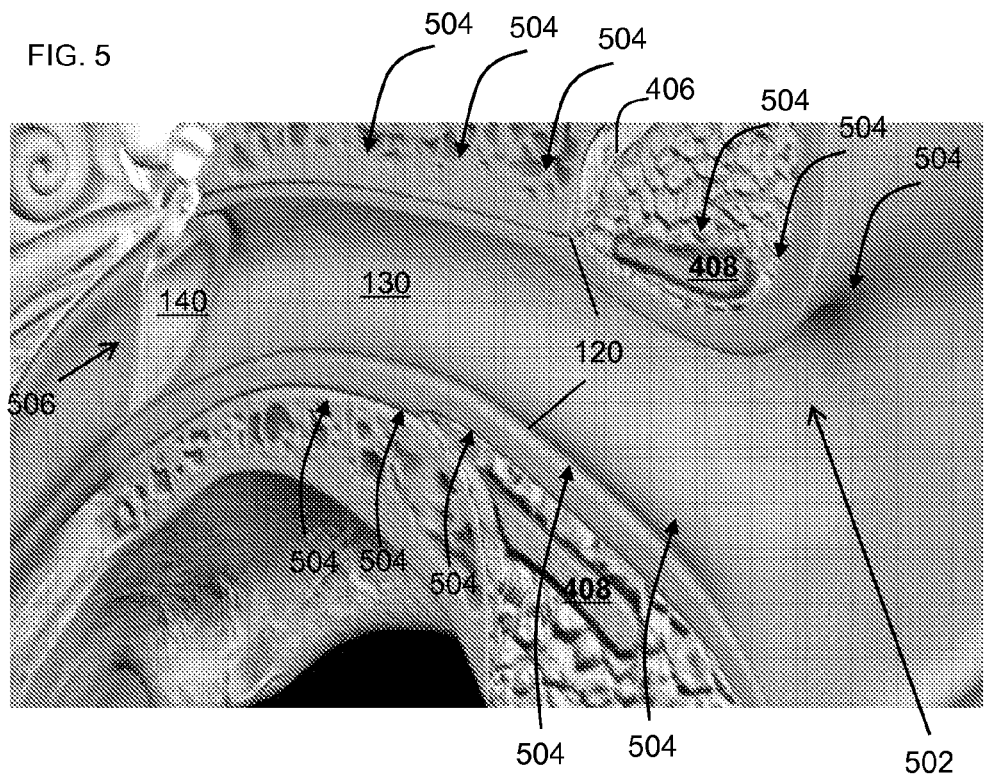
FIG. 5 is a cross sectional view of an ear illustrating sound propagated to the ear canal through the body.

FIG. 5 is a cross sectional view of an ear illustrating sound propagated to the ear canal through the body. The ear canal 130 is an acoustic channel for coupling sound to tympanic membrane 140. Sound reaches ear canal 130 through several paths. The principal path 502 for sound to enter ear canal 130 is through the ear canal opening in the outer ear.

Two other paths are illustrated that can provide sound into ear canal 130. Both paths are through the body and the path is not directly connected to the ambient environment. A path 504 provides sound through bone conduction. For example, sound generated when a person speaks vibrates bone adjacent to ear canal wall 120. The vibration corresponding to the speech is radiated through ear canal wall 120 by this secondary path and into ear canal 130. Similarly, a path 506 can provide sound to ear canal 130 from areas of the inner ear.

The sound provided through paths 504 and 506 is not significant under normal conditions where sound is coupled through the ear canal opening. Conversely, sealing the opening to ear canal 130 prevents sound from the ambient environment from entering. Under this condition the remaining portion of the ear canal is isolated from the ambient environment. The deleterious effect of sealing the ear canal manifests itself when a person speaks. Normally, speech radiates from the mouth and into a person's ears. Many of the high frequency components that we utter are generated by the complex interactions as the sound leaves our mouth. These high frequency components are missing when the speech is radiated through the body (e.g. bone conduction) and into ear canal 130. The sound is further modified due to resonance in the sealed ear canal volume that amplifies (typically <500 Hz) or attenuates frequencies. The resonance in the ear canal volume modifies sound such as our voice making it unfamiliar which can be disconcerting to some people. The sound of bone-conducted speech into the ear canal is often described as lower in frequency, boomy, and muffled. Other sounds which we normally do not hear such as chewing or teeth grinding can become much more prominent when the ear is sealed. The phenomenon of resonance boosting a low frequency signal in a sealed ear canal is known as the occlusion effect. The frequency where the occlusion effect occurs is as a function of the shape, volume, and other physical attributes of the ear canal. Although the occlusion effect varies from individual to individual it typically occurs at frequencies less than 1 kilohertz and, is usually centered around 500 hertz.

Figure 6:
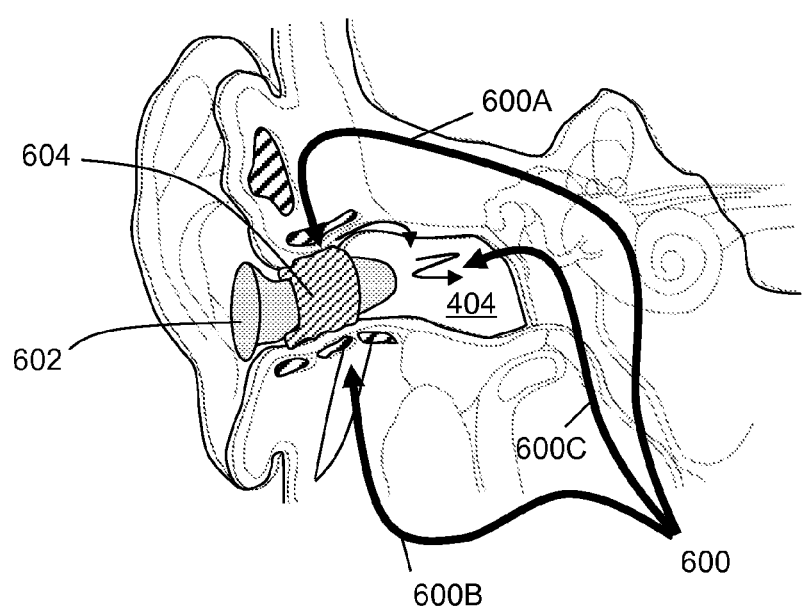
FIG. 6 illustrates a sealed or occluded ear canal in accordance with at least one exemplary embodiment.

FIG. 6 illustrates a sealed or occluded ear canal in accordance with at least one exemplary embodiment. A sealing section comprises an insertion element 602 and an expandable element 604. In a non-limiting example, insertion element 602 is a flexible element that aids in the insertion process to place expandable element 604 in an appropriate location in the ear canal. Typically, insertion element 602 is inserted centrally into the ear canal such that it does not come into contact with the ear canal wall. Insertion element 602 comprises a soft and flexible material that readily bends when contacting the ear canal wall to prevent pain or discomfort. In at least one exemplary embodiment, the length of insertion element 602 is designed so it cannot come in contact with the tympanic membrane when placed in the ear canal.

Expandable element 604 is attached to insertion element 602. Expandable element 604 is typically in a non-expanded state during insertion. In a non-limiting example, expandable element 604 is positioned on insertion element 602 such that it is positioned with its leading edge approximately half way into an average ear canal when insertion element 602 is fully inserted wherein ear canal volume 404 remains. After insertion, expandable element 604 is expanded in the ear canal and touches and forms an acoustic seal with the ear canal wall. Insertion element 602 and expandable element 604 seal an ear canal opening.

Typically, expandable element 604 contacts both the cartilaginous region and the bony region of the ear canal wall for an average user. A person with a short ear canal can have a majority or all of expandable element 604 contacting the bony region of the ear canal. Conversely, a person with a long ear canal can have a majority or all of expandable element 604 contacting the cartilaginous region of the ear canal. Ear canal volume 404 will vary from person to person. In all cases, expandable element 604 seals the ear canal and is comfortable for extended use over long periods of time. In at least one exemplary embodiment, insertion element 602 and expandable element 604 can be designed to be deeply inserted into the ear canal. For example the length of insertion element 602 can be increased to extend deep into the ear canal. Alternatively, the expandable element 604 can extend beyond insertion element 602 deep into the ear canal when expanded. It should be also noted that insertion element 602 can include an instrument package for holding components such as transducers or electronic components.

As mentioned previously, ear canal shape and sizes can vary substantially over a large population. Insertion element 602 and expandable element 604 are designed to fit in a small ear canal opening. Expandable element 604 can then be expanded in size to seal a large or small ear canal size. Thus, insertion element 602 and expandable element 604 combine to form a component that can comfortably seal and fit a large percentage of the population. In at least one exemplary embodiment, expandable element 604 is conformal to an ear canal surface allowing a seal to be formed even if the surface is irregular in shape. A force is applied to a surface of expandable element 604 conforming and holding the surface against the ear canal wall while in use. The force is removed when the expandable element 604 is removed from the ear canal to promote easy removal.

Insertion element 602 and expandable element 604 seal an opening to the ear canal forming the ear canal volume 404 that is isolated from the ambient environment. In general, the sealing section attenuates acoustic information from the ambient environment. Sound can also couple to ear canal volume 404 through the body. Paths 600 illustrate areas where sound can enter. Paths 600A and 600B are bone conduction paths into ear canal volume 404. Path 600C is another path through non-bony structures such as the tympanic membrane. In at least one exemplary embodiment, the surface of expandable element 604 in contact with the ear canal wall reflects sound away from ear canal volume 404 thereby reducing the amount of sound coupled through path 600 into the ear canal.

Figure 7:
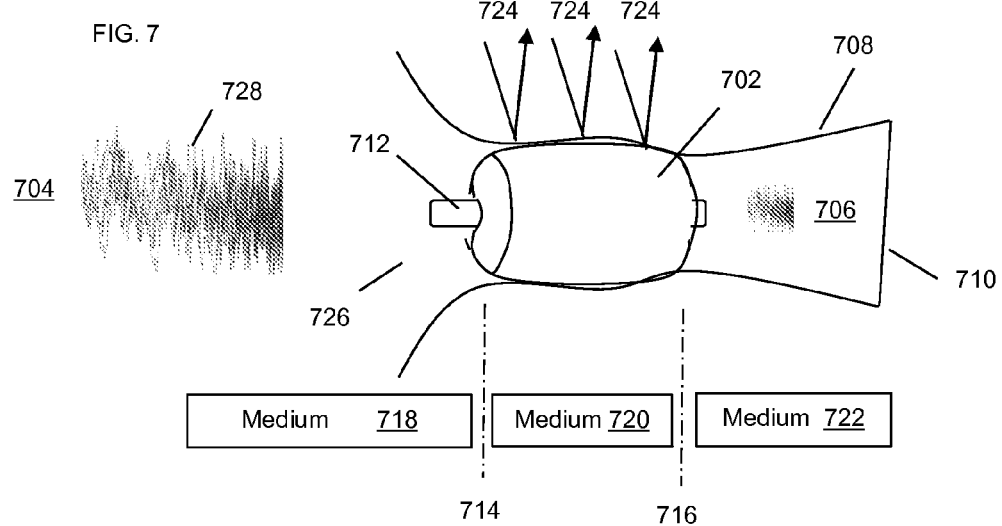
FIG. 7 is an illustration of an expandable device in an ear canal in accordance with at least one exemplary embodiment.

FIG. 7 is an illustration of an expandable device 702 in an ear canal in accordance with at least one exemplary embodiment. Expandable device 702 is inserted in an opening of the ear canal and expanded to seal the ear canal from an ambient environment 704. An ear canal volume 706 is a remaining portion of the ear canal between a distal end of expandable device 702 and a tympanic membrane 710. Expandable device 702 can be designed to take up a predetermined percentage of the total ear canal volume (from a minority to majority portion). As shown, expandable device 702 takes up approximately half of the total ear canal volume.

Painful pressure (unless released) can build up in ear canal volume 706 if expandable device 702 were inserted in an expanded state. Inserting without sealing and then expanding expandable device 702 to seal the ear canal reduces pressure from building up in ear canal volume 706. A valve (not shown) can also be provided that equalizes pressure in ear canal volume 706 and ambient environment 704 when a pressure difference occurs.

In at least one exemplary embodiment, expandable device 702 is a sealed structure that can be filled with a gas, liquid, or gel to increase volume such that the ear canal is sealed. The sealed structure can be a fixed volume or variable volume. In either a fixed volume or variable volume scenario, expandable device 702 is designed to be inserted in a small ear canal and can be expanded to fit a large ear canal thereby providing an ear canal sealing solution that covers a majority of the population. For example, a fixed volume balloon has a maximum volume designed to seal a large ear canal. The fixed volume balloon would then seal smaller ear canals requiring much less volume than the maximum volume available. Conversely, a variable volume balloon can expand or contract to the size of the ear canal from small to large. Thus, the volume of the balloon is variable. In either case, a surface of expandable device 702 is expanded to come into contact with an ear canal wall 708 of the ear canal.

There are several subjective parameters that must be met if expandable device 702 is going to achieve mainstream adoption. In general, expandable device 702 is a sealing section of an earpiece that can comprise other components (e.g. electronics, pumps, transducers, etc.) depending on the application. An earpiece is typically worn over extended periods of time. For example, eight or more hours per day. The sealing section has to be comfortable to a user. Another factor is that expandable device 702 cannot look imposing to someone placing it in their ear. In-ear devices are currently not prevalent in the market place. People may have a concern about using an in-ear device since it is unfamiliar. Thus, this negative bias can be minimized if expandable device 702 looks innocuous.

Expandable device 702 comprises a proximal surface that is directed towards ambient environment 704, a distal surface that is directed towards tympanic membrane 710, and a sidewall surface. Expandable device 702 is expanded radially until the sidewall surface contacts ear canal wall 708 and seals the ear canal. The sidewall surface of expandable device 702 is flexible and will conform to an irregular surface of ear canal wall 708 to form an acoustic seal. In at least one exemplary embodiment, the force at which the surface of expandable device 702 contacts ear canal wall 708 can be adjusted. A maximum force applied by expandable device 702 is limited to a force that will not be painful or uncomfortable to a user that has been generated by subjective measurements among a large population pool. A regulation device such as a pressure valve limits the force that can be applied.

In a non-limiting example, expandable device 702 is a balloon structure. A stent 712 includes one or more channels for providing or removing a gas, liquid, or gel to expand or contract expandable device 702. In at least one exemplary embodiment, a pump (not shown) can be used to provide or remove the medium, which fills expandable device 702. As shown, the proximal and distal surfaces are attached to stent 712 to form a sealed structure. Stent 712 can also have acoustic channels with ports at either end. The ports on the distal end of stent 712 couple to ear canal volume 706. The ports on the proximal end can couple to devices such as transducers (for providing or receiving sound) or passively couple to ambient environment 704. Alternatively, an instrument package can also be formed in stent 712. The instrument package can include electronics, transducers, or other devices that would benefit from being in close proximity to ear canal volume 706. Wires or other interconnect would extend from a port on the proximal end of stent 712 to be coupled to other devices. The balloon surrounding the instrument package and portions of stent 712 would provide further protection from an external environment.

Modeling expandable device 702 yields a common textbook problem presented to graduate level acoustic students known as a three medium problem. Three separate volumes are identified having a boundary 714 and a boundary 716. The ambient environment 704 is a gaseous medium 718 (e.g. air). The ambient environment 704 is bounded by the proximal surface of expandable device 702. The medium (e.g. gas, liquid, gel) used to expand expandable device 702 is a medium 720. The ear canal volume 706 is bounded from medium 720 by the distal surface of expandable device 702. The medium 722 in ear canal volume 706 is a gaseous medium 718 (e.g. air).

The problem addresses how much of the sound 728 in ambient environment 704 passes through expandable device 702 and into ear canal volume 706. In other words, the sound isolation properties of expandable device 702. An additional factor is that the proximal and distal surfaces of expandable device 702 as a balloon comprise a thin membrane or material. For example, in our test studies the balloon comprised a thin layer (less than 0.01 inches) of silicone or urethane material. Furthermore, the proximal and distal surfaces of the balloon would be thinner when expanded. In a non-limiting example of a gas filled variable volume balloon the material thickness of the balloon membrane can change from a thickness of 0.01 inches (un-inflated) to 0.002 inches inflated and contacting ear canal wall 708. In this example, the balloon pressure is greater than atmospheric and the balloon surfaces are under tensile stress. As commonly taught, the thin membrane would act as a low pass filter that would permit sound to pass from medium 718 to medium 720 and from medium 720 to medium 722. Thus, the prevailing theory would indicate that transmission loss from ambient environment 704 to ear canal volume 706 would be poor using expandable device 702.

A device as disclosed hereinabove was built and tested. Several unexpected results were measured and will be discussed in more detail hereinbelow. Tube measurements corresponding to the three medium problem using a pink noise source measured up to 40 dB attenuation in the frequency band for human hearing. Measurements were taken with expandable device 702 filled with a fluid and a gas. Attenuation differences were measurable depending on the medium (e.g. gas or liquid) placed in expandable device 702 but the difference was small in relation to the overall attenuation achieved by the device. Another unexpected result was that the attenuation was a function of the force applied to the surface of expandable element 702 on ear canal wall 708. The attenuation increased with rising force applied to the surface. For example, using a gas (air) to expand expandable device 702 saw a relationship between increasing attenuation with increasing pressure in expandable device 702.

Another unexpected result was the reduction in occlusion effect using expandable device 702. As mentioned above, the occlusion effect is noticeable when the ear is sealed and the person speaks. The sound in the ear canal is often unintelligible due to resonances in ear canal volume 706 and the predominance of low frequency sound. The low frequency sound from the voice is coupled to ear canal volume 706 through bone conduction and through other body paths. It should be noted that the normal path for hearing the human voice is blocked/attenuated by expandable device 702.

The sidewall surface of expandable device 702 is under tensile stress. For example, when expanding expandable device 702 with a gas the interior volume was pressurized to 1.2 atmospheres. The internal pressure not only applies a force pressing the sidewall surface to ear canal wall 708 but also puts the surface under tension. The sidewall surface of expandable device 702 acts as a reflective surface to reflect bone or body conducted sound 724 away from ear canal volume 706 thereby reducing the occlusion effect. This has enormous consequences in being able to provide a legible voice signal from within a sealed ear canal. Similarly, the proximal surface of expandable device 702 is also under tensile stress. Ambient sound 728 entering the ear canal is reflected 726 by the proximal surface. Measurements indicate that acoustic reflectivity greater than 90% can be achieved by using a thin walled membrane under tension for frequencies in the human hearing range.

Figure 8:
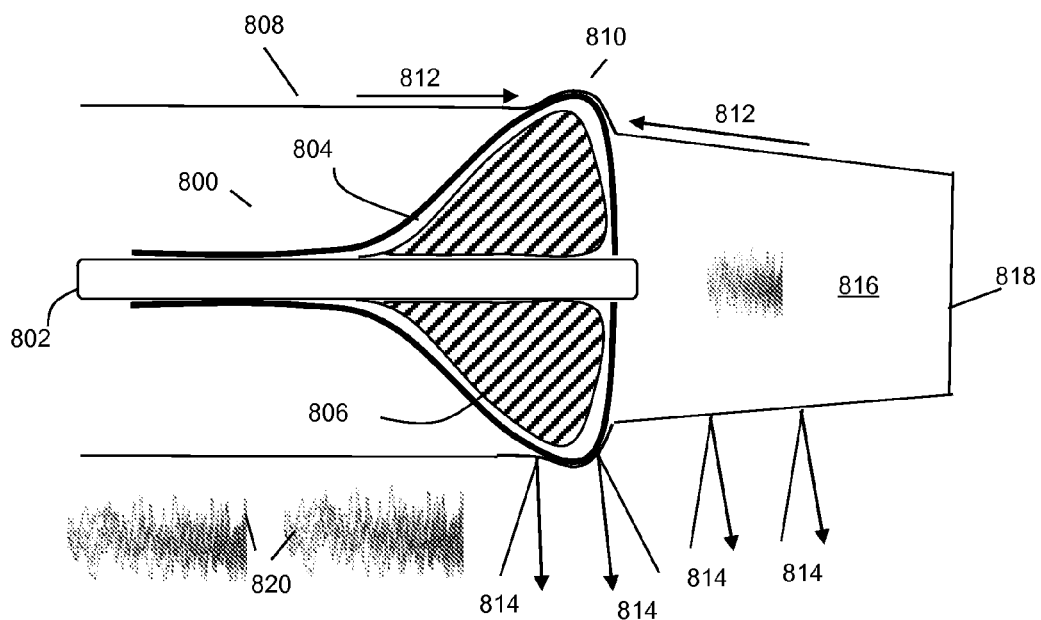
FIG. 8 is an illustration of an expanded conical shaped balloon in contact with an ear canal wall in accordance with at least one exemplary embodiment.

FIG. 8 is an illustration of an expanded conical shaped balloon 800 in contact with an ear canal wall 808 in accordance with at least one exemplary embodiment. Conical shaped balloon 800 is attached to stent 802. Stent 802 can have one or more channels for providing a path for providing and removing medium 806 (a gas, liquid, or gel) for expanding and contracting the device. Stent 802 can also have one or more acoustic channels coupled to ear canal volume 816. Conical shaped balloon 802 seals the ear canal forming an ear canal volume 816. Ear canal volume 816 is bounded by a distal surface of balloon 800, tympanic membrane 818, and ear canal wall 808.

The conical shaped balloon 800 differs from the oval shaped balloon of FIG. 7 having a reduced contact area for sealing the ear canal and forming an ear canal volume 816. It should be noted that the amount of contact area can be varied by molding the conical balloon shape to have an elongated contact area. The conical balloon shape has the contact area towards the distal end of the balloon. In a non-limiting example, conical shaped balloon 800 illustrates a tensioning effect on the skin of the ear canal when a force is applied by a balloon surface 804. The outward force applied by the balloon surface 804 in an area 810 of ear canal wall 808 deforms the skin layer. The ear canal wall skin layer is elastic and stretches since the surface area of the ear canal wall 808 has been increased by the deformation. The stretching of the ear canal wall skin layer due to deformation is indicated by arrows 812 and would occur circumferentially around ear canal wall 808. In general, the thick skin layer in the cartilaginous region would deform more than the thin skin layer in the bony region of the ear canal.

As mentioned previously, balloon 800 has a thin membrane that is under tensile stress pressed against ear canal wall 808 that seals ear canal volume 816 from the ambient environment. A portion of the sound normally conducted through bone and other internal paths (e.g. speech, chewing, etc.) into ear canal volume 816 is reflected away from the ear canal thereby reducing the occlusion effect. The amount of occlusion effect mitigation could not be entirely attributed to reflection by balloon 800. The process of stretching ear canal wall 808 using balloon 800 further mitigates the occlusion effect. Deformation of ear canal wall 808 places the skin layer and underlying tissues under tensile stress much like the head of a drum. Similar to balloon surface 804, stretched skin layer of ear canal wall 808 is a sound reflective surface. The occlusion effect mitigation from ear canal wall 808 is illustrated by sound 820 coming from the body and being reflected away from ear canal volume 816 as shown by arrows 814. Ear canal volume 816 is a sealed volume that has resonances that can increase the amplitude of certain frequencies while reducing others. As described above, this is most noticeable with a sealed ear canal and user speech. Measurements and subjected testing have conclusively shown that reducing the amount of body-conducted sound to ear canal volume 816 substantially decreases the occlusion effect.

Another aspect of creating an acoustic seal in the ear canal is that it is also a watertight seal. People who are prone to ear infections or spend a lot of time in water such as a swimmer wear earplugs. In a non-limiting example, balloon 800 can be used as an earplug for preventing a liquid from entering the ear canal. For example, prior to an event where a liquid can enter the ear, a user places a balloon 800 in each ear, inflates balloon 800 to seal the ear canal, and then engages in the event. After finishing the event the user deflates balloon 800 and removes balloon 800. Balloon 800 will have prevented the ear canal from getting wet. In at least one exemplary embodiment, balloon 800, balloon valving, and balloon pump are housed together in a single unit for ease of use.

A problem with many earpieces having an in-ear device is maintaining the seal over an extended period of time under a wide variety of conditions. In particular, stability of the earpiece when a person is moving such as running or exercising is difficult to achieve. As disclosed above, ear canal wall 800 is slightly deformed by the internal pressure that provides a radial force that pushes surface 804 against ear canal wall 808. The deformation makes it difficult to dislodge balloon 800 even under vigorous movement. Moreover, in testing, balloon 800 is able to support a typical housing having electronics, transducers, battery, and other components for an earpiece without breaking the seal and maintaining a high level of comfort. Thus, deforming ear canal wall 808 circumferentially in the ear canal is a very stable method for holding an earpiece in place.

FIG. 9 is a graph 900 illustrating sound isolation as a function of inflation of an inflatable system in accordance with at least one exemplary embodiment. The inflatable system as disclosed hereinabove, seals an opening of an ear canal isolating the remaining ear canal volume from the ambient environment. The measurement is made in a tube. An inflatable system is inserted in the tube forming a first region, the balloon, and a second region. In the first region of the tube, pink noise 902 is provided to a first side of the inflatable system that is measured by a microphone. In the second region that is isolated by the inflatable system a second microphone takes measurements. The amount of sound isolation provided by the inflatable system is the difference in the measured sound levels in the first and second regions. The tube in the second region is extended to a length where signal reflection is not a measurement issue (e.g. there is no reflected signal received by the second microphone). Additionally, the inflation medium can be a liquid, gas, gel, or other medium to increase/decrease the pressure within the inflatable system to form a seal that isolates the second region from the first region.

In at least one exemplary embodiment, the inflatable system is a gas filled balloon. The diameter of the balloon increases as it is inflated. The balloon creates an acoustic seal when the balloon surface contacts the tube wall. Raising the pressure within the balloon increases the radial force pressing the balloon surface against the tube wall.

The curve 904 represents the measurement when the inflatable system is not completely sealed. Prior to an acoustic seal being formed, a portion of pink noise 902 passes through openings coupling the first region to the second region. The measured signal in the second region will vary in intensity across the frequency band. The portion of curve 904 that is above the pink noise signal is due to resonance 906 in the second region. As shown, both the low frequency and high frequencies are attenuated in the second region.

A curve 908 represents the inflatable system at a first pressure P1 greater than or equal to a seal pressure where the inflatable system has conformed to the inside of the tube. There is a distinct drop in the sound pressure level measured in the first region than the sound pressure level measured in the second region when the inflatable system forms an acoustic seal with the tube. This is indicated by curve 908 being less than curve 902 at all frequencies. Typically, the amount of isolation is not constant but varies over frequency. A curve 910 represents the inflatable system inflated to a second pressure P2 greater than pressure P1. Increasing the pressure in the inflatable system provides improvement of the attenuation properties of the system.

The principal of increasing and decreasing pressure can be used to enhance protection of an earpiece user. The inflatable system can be kept at the sealing value pressure (or slightly greater) under normal operating conditions to maximize comfort to the user. For example, minimum pressures can be used under moderate noise levels where the measured sound pressure levels and a sound pressure level dose does not indicate a potential harmful situation to the user. Furthermore, an earpiece can have circuitry for measuring sound pressure level. Upon detecting a rise in sound pressure level (e.g. greater than 1 dB) or to mitigate potential hearing damage to the user the inflatable system pressure can be increased to raise the attenuation of ambient noise thereby providing further protection. Conversely, detecting benign conditions in the ambient environment, the earpiece could lower the pressure in the inflatable system. Thus, the level of attenuation can be varied corresponding to pressure within a range that is comfortable to the user.

FIG. 10 is a graph 1000 of sound isolation versus occlusion effect in accordance with at least one exemplary embodiment. The occlusion effect was measured for a sealed ear canal. In general, a sealing section having a surface comprising sound reflective material was held against an ear canal wall. In at least one exemplary embodiment, the sound reflective material was under tensile stress to increase the material reflectivity. The force holding the sound reflective material against the ear canal wall also deforms and stretches the elastic skin layer. The sealing section and the stretched ear canal skin layer reflect sound propagating through the body away from the ear canal.

In a non-limiting example, the sealing section is an expanding device such as a balloon. Graph 1000 shows that the occlusion effect is reduced as attenuation is increased. Conversely, the occlusion effect increases as the attenuation decreases. As disclosed above, increasing pressure of the balloon increases attenuation between the ambient environment and the ear canal. Increasing pressure also increases the tensile stress on the surface material of the balloon and further deforms and stretches the ear canal skin layer. The result of which is improved reflectivity of body-conducted sound away from the ear canal thereby reducing the occlusion effect.

Figure 11:
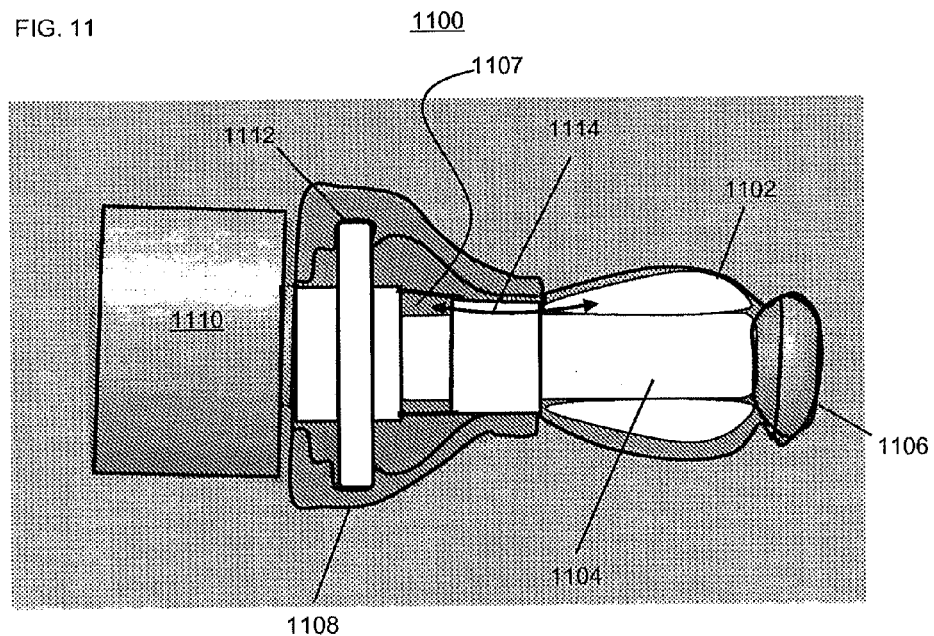
FIG. 11 is an illustration of a passive earpiece for occluding an ear canal and reducing an occlusion effect in accordance with at least one exemplary embodiment.

FIG. 11 is an illustration of a passive earpiece 1100 for occluding an ear canal and reducing an occlusion effect in accordance with at least one exemplary embodiment. Earpiece 1100 comprises an expandable device 1102, a stent 1104, a restoring force device 1108, an end cap 1106, a collar 1114, a stop flange 1112, and a housing 1110. Earpiece 1100 seals an ear canal such that an ear canal volume is formed that is isolated from an ambient environment. Stop flange 1112, a reservoir chamber 1107, restoring force device 1108, and expandable device 1102 combine to reflect and absorb acoustic energy directed to the ear canal opening. Expandable device 1102 also prevents body propagated sound from entering the ear canal volume thereby reducing the occlusion effect.

In at least one exemplary embodiment, stent 1104 is a flexible support structure for mounting expandable device 1102. Stent 1104 aids in directing expandable device 1102 into an ear canal opening. Although stent 1104 is shown as being straight it should not be limited to this shape and can be formed having one or more curves or angles to simplify insertion into the ear canal. Stent 1104 can also include one or more longitudinal channels formed therein. For example, the channels can be used to acoustically couple the ear canal volume to a transducer for receiving or providing sound. Alternatively, one or more channels can be controllably coupled to the ambient environment for providing ambient sound to the ear canal volume. Conversely, stent 1104 can have no acoustic channels or be used as a conduit for other purposes.

An end cap 1106 is attached to a distal end of stent 1104 and has a diameter greater than stent 1104. End cap 1106 comprises a flexible and soft material that minimizes scratching or pain should it come in contact with the ear canal wall. End cap 1106 can be permanently affixed to stent 1104 or be removable. In at least one exemplary embodiment, end cap 1106 is molded simultaneously with stent 1104. Making end cap 1106 removable allows for simplified cleaning should cerumen build up in a port of an acoustic channel or allow periodic replacement for sanitary reasons. End cap 1106 is also a retaining flange for expandable device 1102.

Stop flange 1112 and collar 1114 are formed overlying stent 1104. Stop flange 1112 is located on a proximal end of stent 1104 nearest the ambient environment when inserted. Stop flange 1112 limits insertion depth into an ear canal. The diameter of stop flange 1112 is larger than a large ear canal opening. Thus, the maximum distance of insertion is from a distal surface of stop flange 1112 to end cap 1106. Collar 1114 is between end cap 1106 and stop flange 1112 on stent 1104. Collar 1114 is a mounting point for expandable device 1102 and restoring force device 1108. Collar 1114 also couples expandable device 1102 to restoring force device 1108. In at least one exemplary embodiment, stop flange 1112, collar 1114, end cap 1106, and stent 1104 are molded as a single piece. Alternatively, collar 1114 and stop flange 1112 can be formed as separate pieces. Collar 1114 can be positioned on stent 1104 and attached by adhesive, welded or other means. Stop flange 1112 can then be attached to the proximal end of stent 1104 by a similar method. A housing 1110 is coupled to stop flange 1112. Housing 1110 can house components of earpiece 1100 such as electronic and mechanical devices of the system.

Expandable device 1102 comprises an expandable membrane that is attached to collar 1114 and stent 1104. Restoring force device 1108 also comprises an expandable membrane. Restoring force device 1108 is attached to collar 1114 and stop flange 1112. In at least one exemplary embodiment, the membrane of restoring force device 1108 is more elastic than the membrane of expandable device 1102. Expandable device 1102 and restoring force device 1108 comprise pressurized volumes that are coupled together via collar 1114. The medium filling the volumes can be a gas, liquid, or gel.

Earpiece 1100 is designed to fit a large cross-section of the population. The diameter of expandable device 1102 is greater than a statistically large ear canal diameter. The membrane of expandable device 1102 is flexible and conforms to the shape of the ear canal. The medium in expandable device 1102 is displaced to restoring force device 1108 to conform to the smaller diameter of the ear canal. An increase in volume in restoring force device 1108 results in a corresponding rise in pressure. The pressurized medium within restoring force device 1108 is coupled to expandable device 1102 via collar 1114 such that a radial force is applied on the membrane forming an acoustic seal with the ear canal wall. Thus, inserting earpiece 1100 into a small ear canal will displace the greatest amount of the medium from expandable device 1102 resulting in the highest radial force applied against the ear canal wall. Conversely, a large ear canal will result in the weakest radial force. In at least one exemplary embodiment, earpiece 1100 can be optimized for different sized ear canals. For example, expandable device 1102 can be designed for small, medium, and large ear canals to reduce the variation in radial force and tensile stress that is applied to the membrane of expandable device 1102.

In at least one exemplary embodiment, earpiece 1100 is a passive device such that the user does not change the pressure in expandable device 1102. The initial pressure in expandable device 1102 and restoring force device 1108 is fixed when the unit is made. Alternatively, earpiece 1100 can have a port for coupling to a pump to increase pressure in expandable device 1102 and restoring force device 1108 within a predetermined range. An over pressure valve can be provided that prevents a predetermined maximum pressure from being exceeded.

Subjective measurements with a number of test subjects have shown a pressure greater than 1.3 bar (at seal level) should not be exceeded for a fixed volume device inflated to occlude an ear canal. A fixed volume device will not expand above a predetermined volume. The shape of the volume was spherical for the subjective measurements. The diameter of the sphere is designed to be greater than a statistically large ear canal. The fixed volume device is inserted into the test subject ear canal and expanded to occlude the ear canal. Further pressurization of the fixed volume device increases the force applied by the membrane of the fixed volume device against the ear canal wall. It was found that the pressure applied to the ear canal walls (e.g. above 1.3 bar at sea level) can stimulate the ear canal wall nerves causing discomfort or pain. In a non-limiting example, the pressure differential between an expandable device for ear occlusion and the ambient is kept at 0.2 bar or less to ensure that a large portion of the population will not feel any discomfort having the device in their ear over an extended period of time.

A variable volume expandable device has also been subjectively tested for comfort. The variable volume expandable device is not constrained from expanding as pressure increases due to the elasticity of the membrane material. Under equal internal pressure conditions, a variable volume device will apply less force on the membrane than a fixed volume device to the ear canal wall. This is partly due to the elasticity of the membrane material and the fact that the membrane has areas where it is not constrained. For example, the surface of variable volume device facing the tympanic membrane is unconstrained. The membrane is free to expand in this region. This results in the variable volume device testing subjectively better from a comfort perspective than the fixed volume device at equal pressures.

Figure 12:
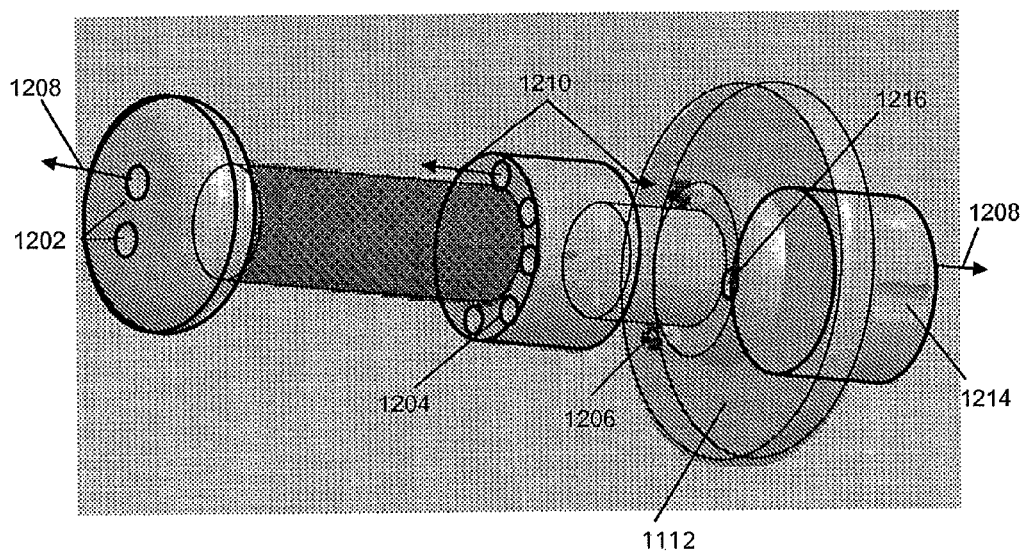
FIG. 12 is an illustration of a stent and stop flange in accordance with at least one exemplary embodiment.

FIG. 12 is an illustration of stent 1104 and stop flange 1112 in accordance with an exemplary embodiment. In a non-limiting example, stent 1104 has two channels extending through the entire length of the structure. End cap 1106 has two port openings 1202 that couple to channels in stent 1102. Arrows 1208 illustrate a channel path through the structure. In at least one exemplary embodiment, the two channels are acoustic channels for an earpiece that directs sound to the ear canal via an ear canal receiver and can monitor sound in the isolated ear canal volume with a microphone. The ear canal receiver and microphone can be coupled to the acoustic channels and housed in housing 1110.

Collar 1114 has openings 1204 that couple the volume of expandable device 1102 to restoring force device 1108. Openings 1204 extend through collar 1114 and are indicated by arrows 1210. Thus, the medium (gas, liquid, or gel) that pressurizes the volumes can freely flow between expandable device 1102 and restoring force device 1108. In at least one exemplary embodiment, a portion of the surface of collar 1114 is formed concave to support an attachment process of expandable device 1102 and restoring device 1108 using shrink tubing.

One-way valves 1206 provide the medium into the volumes of expandable device 1102 and restoring force device 1108. For example, a liquid is provided into the volumes through one-way valves 1206. As the liquid enters it will displace gas (e.g. air) that had previously resided in the volumes. The displaced gas exits through opening 1216. A slot 1214 aligns with a channel through stop flange 1112 that corresponds to opening 1216. An interconnect such as flexible tubing can couple to the channel for removing gas or liquid through a valve. Once filled with the liquid the opening can be plugged or sealed. Providing further liquid through one-way valves 1206 will then pressurize the volumes of expandable device 1102 and restoring device 1108.

Figure 13:
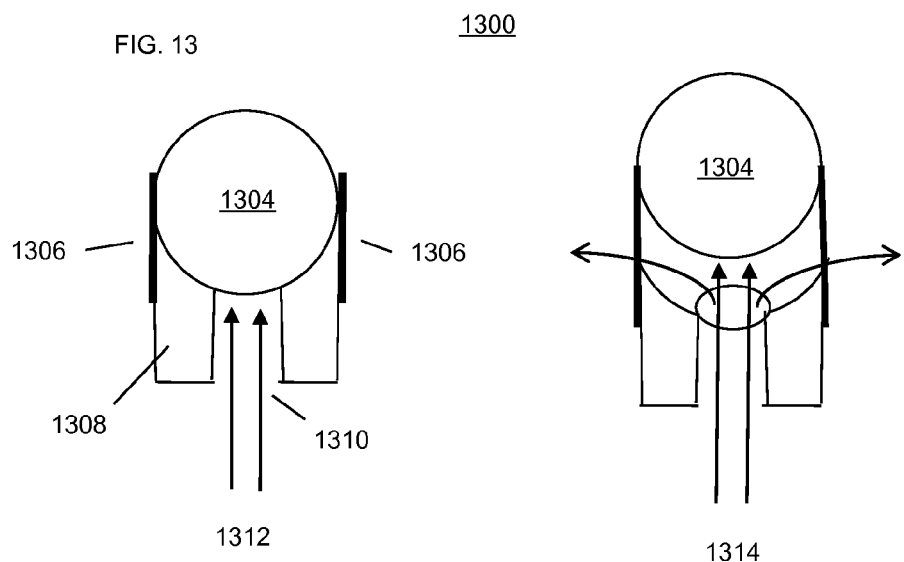
FIG. 13 is an illustration of a one-way valve in a closed and open position in accordance with at least one exemplary embodiment.

FIG. 13 is an illustration of a one-way valve 1300 in a closed and open position in accordance with an exemplary embodiment. One-way valve 1300 has a very small form factor and can be used to provide a medium such as a gas, liquid, or gel to the volumes of expandable device 1102 and restoring force device 1108. One-way valve 1300 comprises a moveable element 1304, a valve base 1308, and holding structures 1306. Base 1308 has an opening 1310 through which the medium such as a gas, liquid, or gel can pass through. Moveable element 1304 mates with a seat on base 1308. Holding structures 1306 are attached to moveable element 1304 and valve base 1308. For example, holding structures 1306 comprise an elastic material under tension whereby moveable element 1304 is held against the seat on base 1308 forming a seal under quiescent conditions.

A medium 1312 provided to valve 1300 does not unseat moveable element 1304 when the force applied by medium 1312 to moveable element 1304 is less than the retaining force of holding structures 1304. One-way valve 1300 opens when a medium 1314 has sufficient force to unseat moveable element 1304 from base 1308. In this condition, the elastic material of holding structures 1306 stretches such that moveable element 1304 does not touch base 1308. The medium 1314 will continue to flow through the opening 1310 and around unseated moveable element 1304 until the force applied by medium 1314 can no longer overcome the retaining force of holding structures 1306 or a force applied to moveable element 1304. For example, pressure in the volume of expandable device 1102 and restoring force device 1108 increases as more of medium 1314 is provided. The pressure applies a force to moveable element 1304 to seal one-way valve 1300. One-way valve 1300 closes and seats to base 1308 when the pressure and holding structures 1308 combine to overcome medium 1314.

Figure 14:
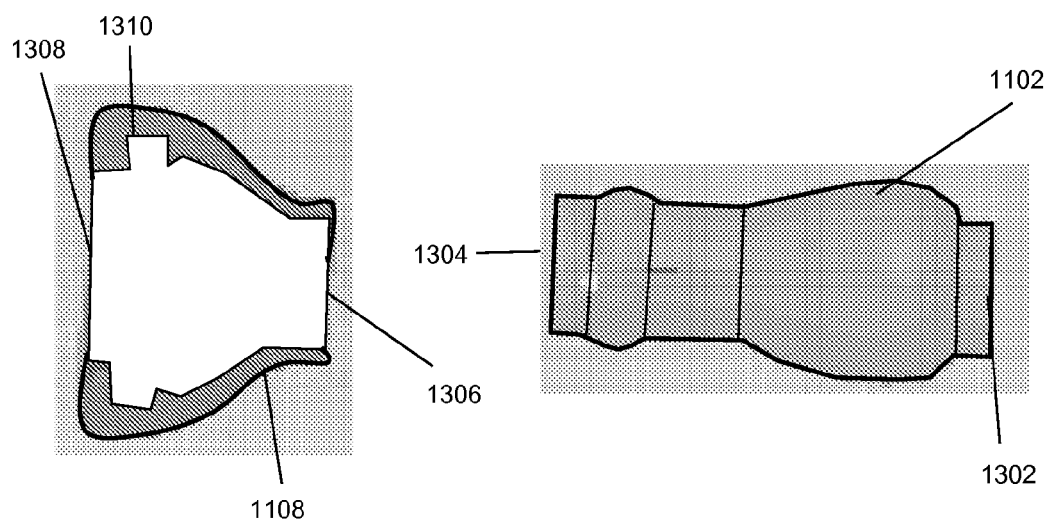
FIG. 14 is an illustration of an expandable device and a restoring force device in accordance with at least one exemplary embodiment.

FIG. 14 is an illustration of an expandable device 1102 and a restoring force device 1108 in accordance with an exemplary embodiment. Expandable device 1102 is a flexible and expandable structure having a distal end opening 1302 and a proximal end opening 1304. Similarly, restoring force device 1108 has a distal end opening 1306 and a proximal end opening 1308.

In at least one exemplary embodiment, restoring force device 1108 is shaped having a groove 1310. Groove 1310 corresponds to stop flange 1112. Restoring force device 1108 can be pulled over stent 1104 such that groove 1310 overlies stop flange 1112 and opening 1306 overlies collar 1114. Groove 1310 retains and aligns restoring force device 1108 onto earpiece 1100. Restoring force device 1108 is sealed to stop flange 1112 and collar 1114 forming a sealed volume. Adhesive, welding, or some other sealing process can be used to attach restoring force device 1108.

Expandable device 1102 can be pulled over stent 1104 such that opening 1304 overlies collar 1114 and opening 1302 is adjacent to end cap 1106. Expandable device 1102 is sealed to collar 1114 and stent 1104 forming a sealed volume. As mentioned previously, the volumes of expandable device 1102 and restoring force device 1108 are coupled together via openings in collar 1114. In an alternate embodiment, expandable device 1102 and restoring force device 1108 can be formed as a single structure. The single structure is pulled over stent 1104. The proximal and distal openings are sealed using adhesive, or welding. Shrink tubing could be placed overlying collar 1114. Shrinking the tubing would seal and retain the structure to collar 1114.

In at least one exemplary embodiment, the material used to form the membrane of expandable device 1102 and restoring force device 1108 is flexible and biologically compatible with skin. In particular, expandable device 1102 must provide a high level of comfort to have broad acceptability with the population. The device can be worn for extended periods of time (e.g. 8 or more hours) over a wide range of physical conditions such as temperature, humidity, rain, wind, and snow. Human factors such as allergies, sweat, cerumen, and strenuous physical movement need to be accounted for. The membrane is pressed against the ear canal wall and the membrane is under tensile stress. The membrane material also needs to be inert to chemicals. It is desirable that the membrane material be capable of retaining a gas, liquid, or gel since leakage would require refilling or result in a loss of performance. In a non-limiting example, materials such as silicone, dimethylsilicone rubber, fluorosilicone, nitrile rubber, natural rubber, polyethylene, butyl rubber, polystyrene, polyethylene, nylon, polyethylene terephthalate, and polyurethane are adaptable for use as a membrane material for an expandable device for occluding the ear and reducing the occlusion effect.

Figure 15:
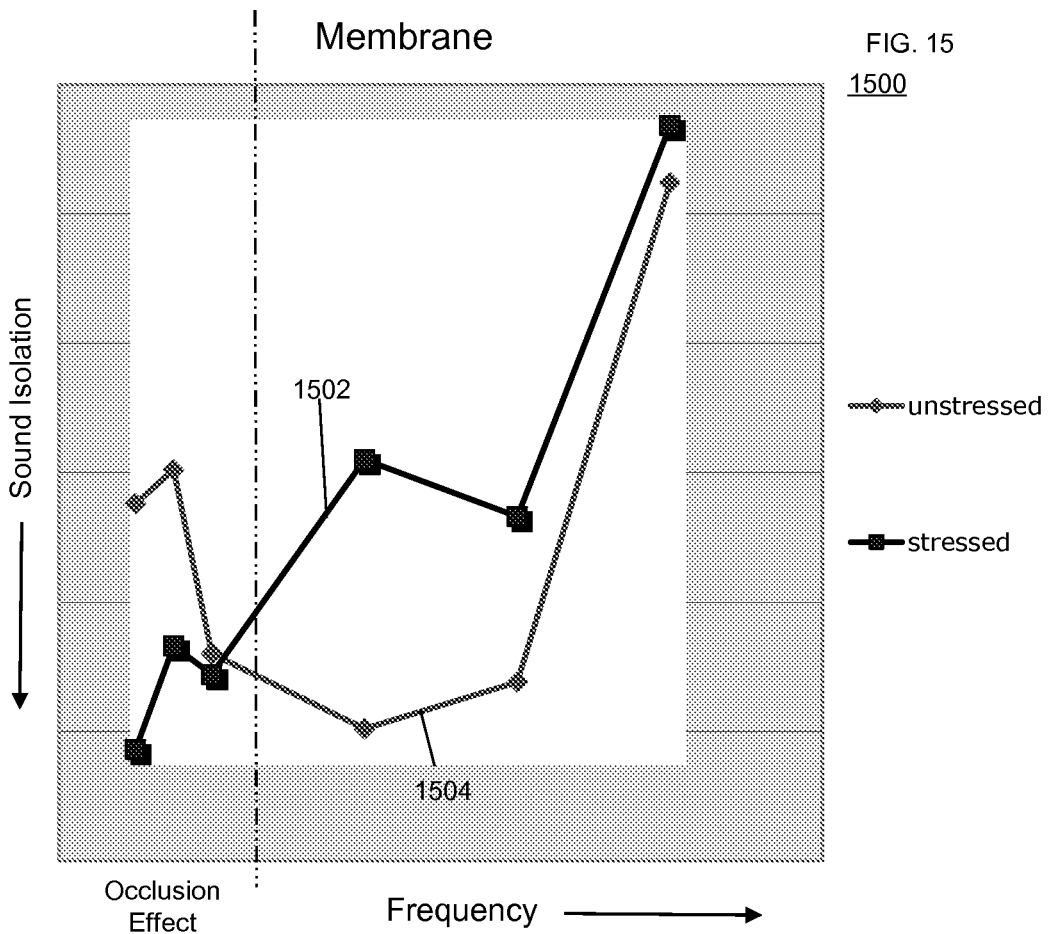
FIG. 15 is a graph of a thin silicone membrane illustrating attenuation when the membrane is stressed and unstressed in accordance with at least one exemplary embodiment.

FIG. 15 is a graph of a thin silicone membrane illustrating attenuation when the membrane is stressed and unstressed in accordance with an exemplary embodiment. In general, graph 1500 shows that specific filter characteristics can be generated by controlling the tensile stress on the membrane material. The stressed membrane 1502 has a high pass filter characteristic. Stressed membrane 1502 has good attenuation characteristics at low frequencies while being transmissive to higher frequencies. Stressed membrane 1502 attenuates by reflecting low frequency acoustic waves. In at least one exemplary embodiment, adjusting the tensile stress on membrane 1502 can control the filter characteristics of stressed membrane 1502. The reflectivity and frequency response to tensile stress is also a function of the initial thickness of the material and the material characteristics.

The occlusion effect typically occurs at lower frequencies in the human hearing range. For example, the occlusion effect occurs at frequencies below 1 khz and peaks at a frequency around 500 hz. Stressed membrane 1502 is adjusted to have maximum attenuation in the frequency range where the occlusion effect occurs. Referring to graph 1500, a region to the left of the dashed line on graph 1500 corresponds to frequencies where the occlusion effect is most prominent for the vast majority of the population. As shown, stressed membrane 1502 has maximum attenuation where the occlusion effect occurs. Thus, placing stressed membrane 1502 adjacent to an ear canal wall where bodily propagated sound normally enters will reflect sound away from the ear canal volume and will have maximum attenuation at frequencies where the occlusion effect normally occurs. It is well known, that the sound of a person's voice with the ear occluded sounds unnatural. Stressed membrane 1502 having low pass characteristics as shown on graph 1500 allows higher frequencies into the ear canal volume that make user speech sound more natural with the ear occluded.

Conversely, measurements taken when the membrane was unstressed (or under low stress) show a low pass filter characteristic. In graph 1500, unstressed membrane 1504 has reduced attenuation at frequencies where the occlusion effect occurs. Thus, in the range where the occlusion effect occur are attenuated less than stressed membrane 1502 and higher frequencies (e.g. to the right of the dashed line) are attenuated more than stressed membrane 1502.

Using a combination of membranes in various states of stress can generate specific filter responses such as a bandpass or notch filter. For example a high pass filter (stressed membrane) allows frequencies to pass below a cutoff frequency. Signals are attenuated above the cutoff frequency. Following the high pass filter with a low pass filter having a cutoff frequency above the high pass filter would result in a bandpass filter between the two cutoff frequencies. A notch filter can be generated by moving the cutoff frequency of the low pass filter below the cutoff of the high pass filter such that the signals between the two cutoff frequencies are attenuated.

Figure 16:
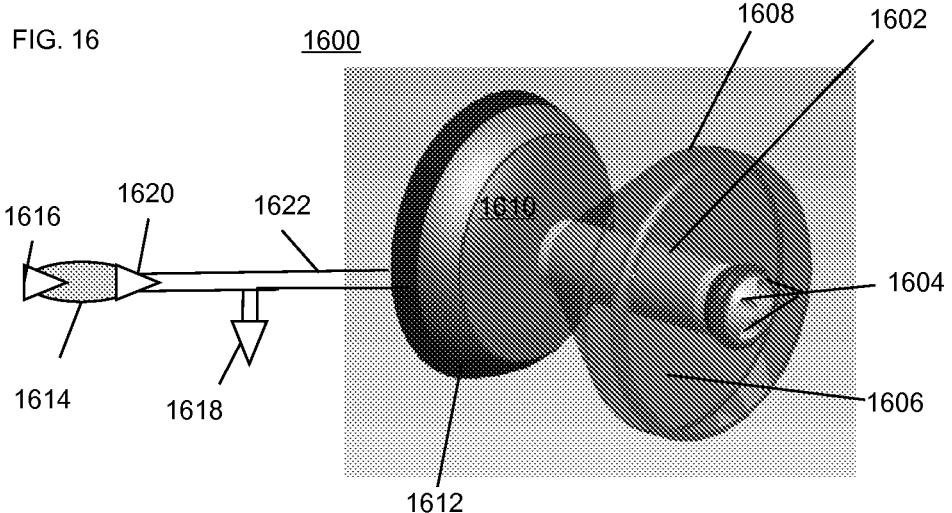
FIG. 16 is an illustration of a sealing section 1600 in accordance with at least one exemplary embodiment.

FIG. 16 is an illustration of a sealing section 1600 in accordance with an exemplary embodiment. Sealing section 1600 comprises a stop flange 1610, a stent 1602, and an expandable device 1606. In general, sealing section 1600 can be used as a stand alone earplug for sound attenuation or as a component of an earpiece system that can perform one or more of the following: receive sound from the ambient environment; receive sound from the ear canal volume; provide sound to the ear canal volume; or modify audio content. Sealing section 1600 isolates the ear canal resulting in the attenuation of sound from the ambient environment and a reduction of the occlusion effect. In particular, sealing section 1600 enables the use of an ear canal microphone in a sealed ear canal volume for transmitting user speech. The sealed ear canal volume has resonance that exacerbates certain frequencies that often render speech unintelligible or different from what is normally heard. Minimizing the occlusion effect by reducing bodily propagated sound entering the ear canal volume makes user speech sound more natural, articulate, clear, and understandable. Using a high pass filter to pass high frequency bodily conducted sounds into the ear canal volume can enhance the naturalness of the sound.

Stent 1602 is a flexible support structure that is used to direct expandable device 1606 into an ear canal. As shown, stent 1602 has one or more channels 1604. In at least one exemplary embodiment, stent 1602 has a channel coupled to an interior volume of expandable device 1606 for providing and removing a medium (gas, liquid, or gel). Stent 1602 can also have channels 1604 on a distal end that couple to the ear canal volume. In a non-limiting example, acoustic channels couple through stent 1602 and are coupled to transducers on a proximal end (closest to the ambient environment) of stent 1602 for providing and receiving sound in the ear canal volume. Alternatively, would not have acoustic channels in an earplug application where noise isolation from the ambient environment is the principal goal.

Expandable device 1606 is attached to stent 1602. In at least one exemplary embodiment, expandable device 1606 is a conical shaped balloon having a sealing sidewall 1608. Sealing sidewall 1608 contacts and conforms to an ear canal wall forming an acoustic seal. The balloon is molded in the conical shape and is a sealed structure. As shown, the balloon is sealed and attached to stent 1602. In at least one exemplary embodiment, expandable device 1606 is a constant volume balloon.

As mentioned previously, stent 1602 has a channel (not shown) coupled to the interior volume of expandable device 1606. In at least one exemplary embodiment, a pump 1614 is coupled to the channel through an interconnect 1622 for providing the medium to expandable device 1606. Pump 1614 is a hand pump that has a one-way valve 1616 and a one-way valve 1620. A third one-way valve 1618 is down stream of pump 1614. In a non-limiting example, air is a medium provided by pump 1614 through the channel to expandable device 1606. Valve 1616 is closed when pump 1614 is squeezed to fill expandable device 1606. Squeezing pump 1614 creates pressure in pump 1614 that opens valve 1620 and provides the displaced volume of air to expandable device 1606. Valve 1620 closes after the air has been pumped out of the body of pump 1614. The pump body then returns to its original shape when released (from being squeezed). Air is provided through valve 1616 from the ambient to fill the pump body. The process can then be repeated to add more air to expandable device 1606. In a non-limiting example, valve 1618 is an over pressure valve and a pressure release valve. Valve 1618 automatically opens when the pressure in expandable device 1606 exceeds a predetermined value. Valve 1618 can also be manually opened to release air from expandable device 1606 thereby reducing the pressure or deflating the structure.

In at least one exemplary embodiment, stop flange 1610 is attached to the proximal end of stent 1602. As it name implies stop flange 1610 limits the depth of insertion of stent 1602 and expandable device 1606 into the ear canal. As illustrated, stop flange 1610 has a diameter greater than a statistically large ear canal. Stop flange 1610 will cover the ear canal opening when inserted and rest in the concha area of the ear. Referring to FIG. 4, a stop flange 414 is illustrated. In this embodiment, stop flange 414 is partially inserted in the ear canal opening. A sidewall of stop flange 414 is radially flexible to accommodate a large percentage of ear canal sizes. The profile of stop flange 414 is tapered to allow partial insertion in a small ear canal while having a large diameter near a proximal end (towards the outer ear) that limits insertion. The sealing section 402 here can couple to one or more housings for mechanical and electrical components.

Referring back to FIG. 16, stop flange 1610 also prevents sound from entering the ear canal. In at least one exemplary embodiment, stop flange 1610 works in conjunction with expandable device 1606 to isolate an ear canal volume from the ambient environment. In a non-limiting example, stop flange 1610 does not seal the ear canal but does partially block the opening. As previously noted, expandable device 1606 acoustically seals the ear canal from the ambient environment. Stop flange 1610 reduces sound from entering the ear canal by providing a surface exposed to the ambient environment that is highly sound reflective. In other words, sound directed to the ear canal from the ambient environment is reflected back into the ambient. Sound that does enter the ear canal is reflected away from the ear canal volume by expandable device 1606. Bodily-propagated sound that enters the ear canal volume between stop flange 1610 and expandable device 1606 is reflected off the conical surface and out of the ear canal through the unsealed ear canal opening.

Referring back to FIG. 4, the ear canal volume 404 can be acoustically isolated by both stop flange 414 and expandable device 410. Sealing the ear canal twice minimizes an opportunity for sound to enter the ear canal. Moreover, expandable device 410 is not solely responsible for both attenuation and mitigating occlusion effect. The reflective properties of expandable device 410 can be optimized to minimize the occlusion effect, maximize speech intelligibility, and make speech received in the ear canal sound normal (as if received from the ambient environment). Referring back to FIG. 16, a sponge plug 1612 can be added to stop flange 1610 at the proximal end of stent 1602 to seal the ear canal opening. A sponge plug 1612 is absorptive to sound. Thus, a combination of sound reflection and absorption is used to minimize sound entering the ear canal. The sponge plug 1612 also absorbs bodily-conducted sound entering the ear canal between the expanding device 1606 and stop flange 1610.

Expandable device 1606 and stop flange 1610 form a very stable platform under a wide variety of user operating conditions. Earpieces are prone to instability during normal human activities such as exercising or other physical activities. For example, many people like to listen to music while exercising. Earpieces are known to fall out of the outer ear during the physical jarring and head movements that are common during exercise. Expandable device 1606 contacts and deforms the ear canal wall. The deformation makes it difficult to pull sealing section 1600 out of the ear. The flexibility of the balloon material is comfortable even under high impact activities. Sealing the outer portion of the ear canal opening with stop flange 1610 further increases the stability of the device to movement even with component housings attached to sealing section 1600. Thus, a system has been provided that maintains a physical contact with the ear canal wall to reduce movement of an earpiece while maintaining comfort and device performance under different operating conditions.

Figure 17:
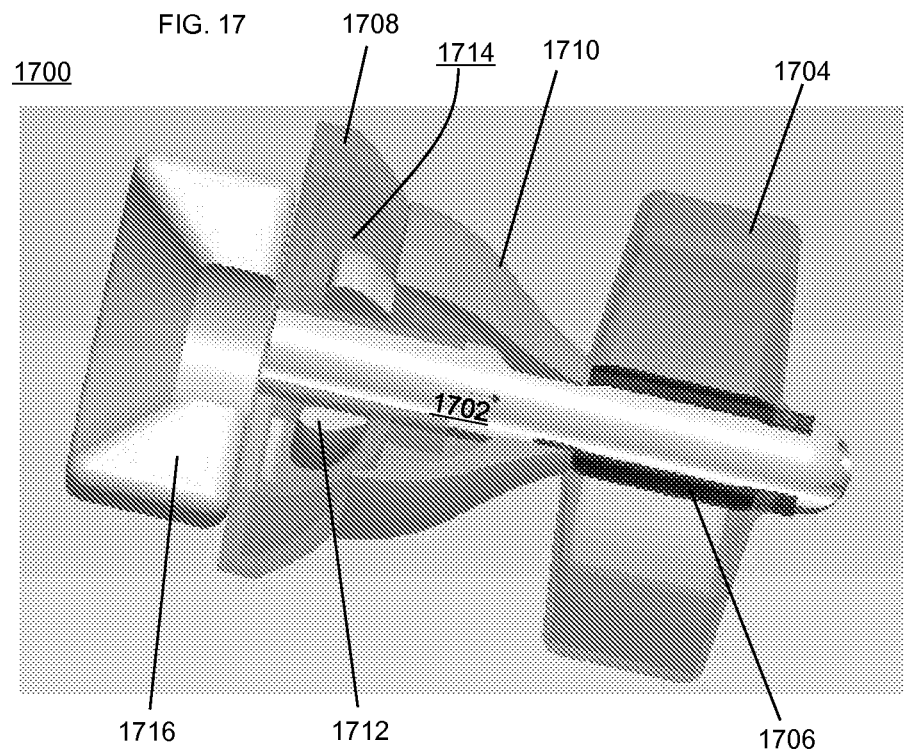
FIG. 17 is a cross-sectional view of a sealing section of an earpiece in accordance with at least one exemplary embodiment.

FIG. 17 is a cross-sectional view of a sealing section 1700 of an earpiece in accordance with at least one exemplary embodiment. Sealing section comprises a stent 1702, an expandable device 1704, a stop flange 1708, a stop flange seal 1710, and a housing 1716. A sealing section is a portion of an earpiece that is inserted in an ear canal. The sealing section creates an ear canal volume that is isolated from the ambient environment. Sealing section 1700 is comfortable, is very stable under a wide variety of physical activities, provides sound isolation from noise in the ambient environment, and reduces the occlusion effect.

Stent 1702 is a support structure for sealing section 1700. Stent 1702 is a flexible structure and can include one or more channels. Expandable device 1704 is attached to a distal end of stent 1702. Stop flange 1708 is attached to a proximal end of stent 1702. Stop flange 1708 has a major surface that is larger than a statistically large ear canal. Stop flange 1708 can be made having a major surface exposed to the ambient environment that is reflective to sound or absorptive to sound thereby reducing sound entering the ear canal. In at least one exemplary embodiment, stop flange 1708 includes a sealing device 1710. Sealing device 1710 seals an ear canal opening as sealing section 1700 is inserted. In at least one exemplary embodiment, sealing section 1700 has more than one ear canal seal to isolate the ear canal volume from the ambient environment. As shown, sealing device 1710 comprises foam that is shaped to be inserted into a wide variety of ear canal openings. The foam compresses to conform and seal the ear canal opening. The foam is absorptive to sound thereby preventing sound from reaching the ear canal or substantially attenuating the sound. Alternatively, sealing device 1710 comprises a structure having conformable/flexible sidewalls similar to that shown in FIG. 4 for sealing the ear canal opening.

Expandable device 1704 comprises a membrane that can be expanded to contact an ear canal wall. For example, the membrane can be a highly elastic material as disclosed hereinabove. The expandable device 1704 can be a variable volume balloon or a fixed volume balloon. Expandable device 1704 is shown in an expanded state. Conversely, a variable volume membrane would collapse to an unexpanded state 1706 when the expanding medium is removed. The form factor of the collapsed variable volume membrane appears to be a part of the stent. In other words, the diameter of stent 1702 is increased merely by the overlying thickness of the membrane. Moreover, stent 1702 and expandable device 1704 looks very innocuous or benign for inserting in the ear. In a non-limiting example, stent 1702 has a diameter of 2.5 millimeters and a length of 15 millimeters from proximal to distal end thereby positioning expandable device approximately half way into an average ear canal. It should be noted that insertion is an issue. Making a device that is not intimidating when being inserted in the ear will greatly increase adoption of an in-ear device.

Stop flange 1708 can have an interior volume 1714 that can house a restoring force device 1712 or a system for expanding/contracting expanding device 1704. In at least one exemplary embodiment, stent 1702 has a channel coupled to expandable device 1704 and to a pump system. The pump system provides a medium such as a gas, liquid, or gel to expand expandable device 1704 to form an acoustical seal in the middle ear. Expandable device 1704 has one or more sound reflective surfaces that reflect sound that has entered through the ear canal opening away from the isolated ear canal volume. Thus, substantial acoustic isolation by sealing the ear canal twice and reflecting or attenuating sound before it can reach the ear canal volume. Expandable device 1704 mitigates the occlusion effect by reflecting bodily conducted sounds away from the ear canal volume and tensioning the ear canal skin layer. Tensioning the ear canal skin layer reflects sound away from the ear canal and can shift the resonance frequency outside the voice range. A housing 1716 can house an instrument package of transducers for coupling to acoustic channels of stent 1702 for providing and receiving sound from the ear canal volume.

In general, sealing section 1700 is inserted into the ear canal with expandable device 1704 in unexpanded state 1706. Stent 1702 directs expandable device into the ear canal. Ideally, stent 1702 and expandable device 1704 in unexpanded state 1706 does not touch the ear canal wall. Sealing device 1710 is pushed into the ear canal opening sealing the ear canal. In at least one exemplary embodiment, sealing device 1710 temporarily retains sealing section 1700 in a fixed position. Expandable device 1704 is expanded to contact the ear canal wall of the middle ear. Expandable device 1704 can contact the cartilaginous region, bony region, or a combination of both regions of the ear canal. In a non-limiting example, the membrane of expandable device 1704 is under tensile stress and contacts at least a portion of the cartilaginous region for comfort and mitigation of the occlusion effect. The radial force applied by expandable device 1704 to the ear canal wall deforms the skin layer and holds sealing section 1700 in place. The combination of expandable device 1704 and sealing device 1710 of stop flange 1708 is very stable and does not move even under vigorous physical activity. Stop flange 1708 is optimized to fit in the concha area of the outer ear that further stabilizes the position of the device. In at least one exemplary embodiment, stop flange 1708 includes a feature that rests against the tragus for retaining sealing section 1700 in place should it move outwardly.

Figure 18:
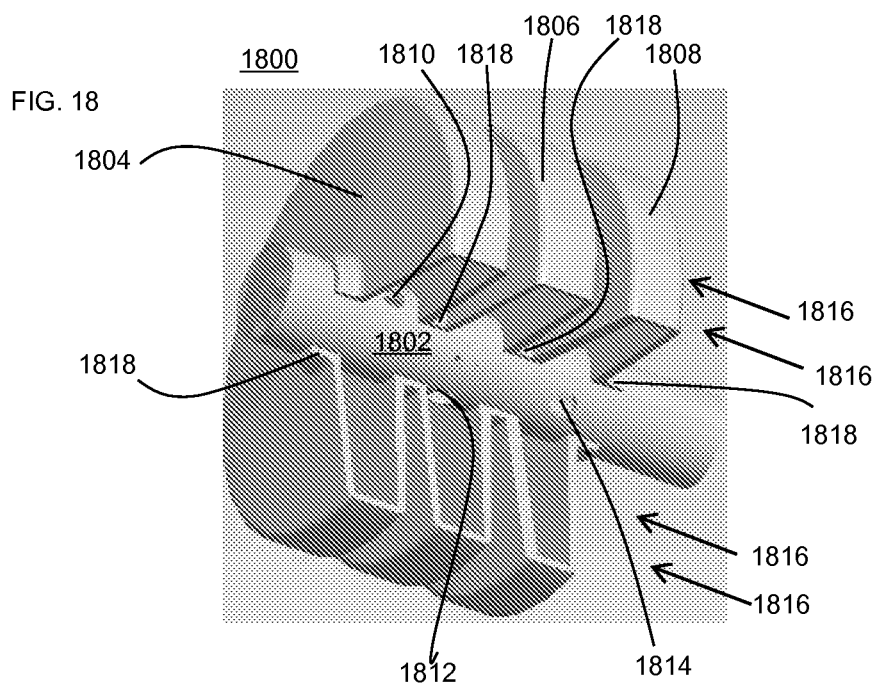
FIG. 18 is an illustration of an expandable device comprising multiple expandable elements in accordance with at least one exemplary embodiment.

FIG. 18 is an illustration of an expandable device 1800 comprising multiple expandable elements in accordance with at least one exemplary embodiment. Expandable device 1800 comprises at least two expandable elements. As shown, expandable device comprises expandable elements 1804, 1806, and 1808. In at least one exemplary embodiment, a stent 1802 is a support structure for expandable elements 1804, 1806, and 1808. Stent 1802 includes at least one channel for providing a medium (e.g. gas, liquid, gel) to expandable elements 1804, 1806, and 1808. In at least one exemplary embodiment, stent 1802 includes a channel for each expandable element. Openings 1810, 1812, and 1814 correspond respectively to expandable elements 1804, 1806, and 1808. Alternatively, a single channel in stent 1802 can couple to openings 1810, 1812, and 1814.

Expandable device 1800 can contact an ear canal wall at one or more points within the middle ear. In a non-limiting example, expandable device 1800 has expandable elements 1804, 1806, and 1808 expanded and contacting the ear canal wall. A membrane of each expandable element contacts and deforms the ear canal wall each forming a separate acoustic seal. Multiple acoustic seals ensure sound isolation even under rigorous physical activity. Sound entering an ear canal is represented by arrows 1816. The membrane of expandable device 1800 reflects sound away from the sealed ear canal volume in a direction opposite of arrows 1816 (e.g. back in the direction of the ambient environment). The ear canal volume is isolated by the six sound reflective membrane surfaces corresponding to three expandable elements 1804, 1806, and 1808 whereas a single expandable device has two reflective membrane surfaces. Thus, expandable elements 1804, 1806, and 1808 form a series of sound isolation devices that progressively isolate the ear canal volume. For example, expandable element 1808 reflects sound from the ambient environment such that a small percentage of the sound is transmitted into the volume between elements 1806 and 1808. Similarly, the sound that had passed through expandable element 1808 is further reduced by being reflected by expandable element 1806 and only a fraction of the sound is transmitted into the volume between elements 1804 and 1806. Finally, the twice-reduced ambient sound is reduced further in amplitude by expandable element 1804. Thus, improved sound isolation is achieved. In a non-limiting example, a reduction in radial force in device 1800 (more comfort) can yield the same or better sound isolation in an ear canal volume when compared to a solitary expandable device structure. Note that sound reflectivity of the membrane can be greater than 90% for the human hearing range with some materials approaching 100% for a specific frequency band.

The sound reflective membranes of expandable elements 1804, 1806, and 1808 contacting the ear canal wall reflect bodily conducted sound away from the ear canal volume thereby mitigating the occlusion effect. Expandable elements 1804, 1806, and 1808 deform the ear canal wall stretching the ear canal skin layer. The ear canal skin layer under tensile stress will reflect bodily conducted sound away from the ear canal volume in areas not contacted by expandable device 1800 further reducing the occlusion effect.

Stability is enhanced by multiple expandable elements. An expandable element 1804, 1806, and 1808 securely anchors the structure in different locations of the ear canal. The force holding the membrane of each element circumferentially against the ear canal wall resists movement due to the friction between the membrane and skin layer. The deformation of the ear canal wall due to the radial force applied by the membrane of each element further prevents movement. Moreover, an ear canal is not regularly shaped or has a constant diameter. Expandable elements 1804, 1806, and 1808 can be situated within the ear canal at different angles and the elements can have different diameters that further secure the structure from moving.

Fluid sealing is also enhanced by having multiple expandable elements. Having more than one ear canal seal prevents liquid from entering an ear canal even if one seal is compromised. As mentioned above, the ear canal is irregularly shaped and varies significantly among the population. Sealing the ear canal in more than one location provides stability such that vigorous physical movement does not shift expandable device 1800. Thus, the membrane to ear canal wall contact is not easily broken thereby maintaining a seal where liquid cannot enter the ear canal volume.

As shown, expandable elements 1804, 1806, and 1808 can be expanded and contracted individually. Channels in stent 1802 couple to a valving system (not shown). The valving system couples to a restoring force device or pumping system for providing or removing the medium to one of or a combination of elements 1804, 1806, and 1808. For example, a person with a short ear canal can utilize only expandable element 1808 for occluding the ear. Expanding elements 1804 and 1806 can contact the bony region of the ear canal wall and could be uncomfortable or produce pain depending on the sensitivity of the canal. Conversely, a person with a long ear canal can utilize element 1804 to occlude the canal deeper into the middle ear. The user also has the ability to try combinations of one or more of expandable elements 1804, 1806, and 1808 to provide the best combination of comfort, sound isolation, mitigation of the occlusion effect, and stability of the device under various operating conditions. In at least one exemplary embodiment, a single expandable element is used in a low noise environment. Upon detecting an increase in ambient sound level additional expandable elements can be expanded to further isolate the ear canal volume and to reduce the occlusion effect for conversations using an ear canal microphone in a noisy environment.

Expandable elements 1804, 1806, and 1808 can be variable volume or fixed volume elements. In at least one exemplary embodiment, elements 1804, 1806, and 1808 are attached to stent 1802 in a single step. In a non-limiting example, a fixed volume structure is formed comprising elements 1804, 1806, and 1808. Stent 1802 is fitted through an opening in the structure and positioned such that openings 1810, 1812, and 1814 align to their corresponding expandable element. The structure is then attached to stent 1802 in regions 1818. In at least one exemplary embodiment, stent 1802 and elements 1804, 1806, and 1808 comprise the same flexible material (e.g. silicone, urethane, or other sound reflective material) to simplify attachment. For example, the material can be welded together or attached with adhesive. The attachment process forms separate sealed elements. Similarly, overlying a flexible membrane circumferentially around stent 1802 can form a variable volume structure. The flexible membrane is attached at locations 1818 to seal the membrane and form separated elements 1804, 1806, and 1808. The medium can be controllably output through openings 1810, 1812, and 1814 to expand the membrane to form elements 1804, 1806, and 1808. In at least one exemplary embodiment, the material thickness of the membrane can be varied to control the direction of expansion of an element.

Figure 19:
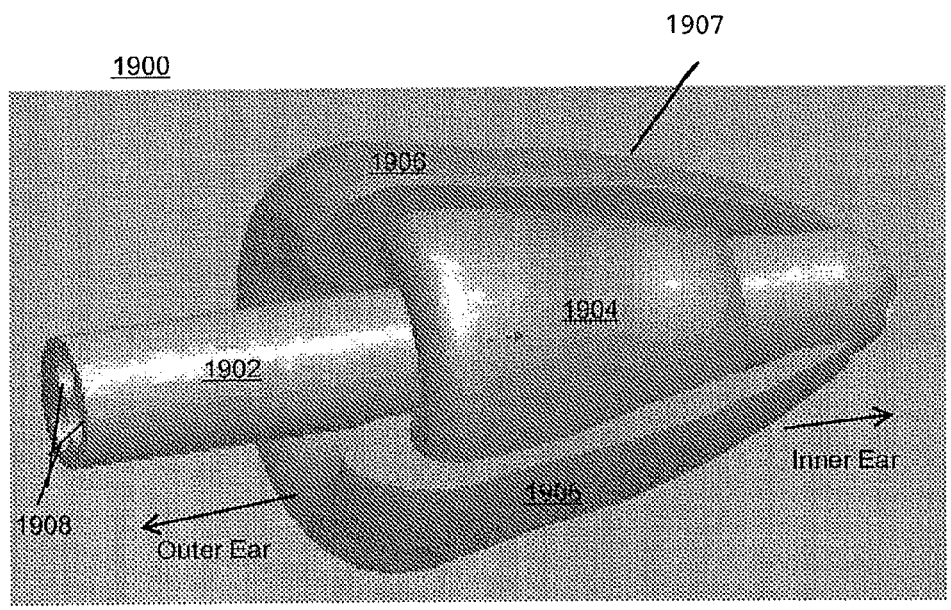
FIG. 19 is an illustration of a foam device for isolating an ear canal volume in accordance with an exemplary embodiment.

FIG. 19 is an illustration of a foam device 1900 for isolating an ear canal volume in accordance with an exemplary embodiment. Foam device 1900 is shown in an unexpanded state suitable for inserting in an ear canal. Foam device 1900 includes a membrane 1907 for reflecting bodily conducted sound when expanded to form an acoustic seal with the ear canal wall thereby isolating an ear canal volume. The membrane 1907 is used to mitigate the occlusion effect by reducing bodily conducted sound reaching the ear canal volume and to reflect sound entering the ear canal opening away from the ear canal volume.

At least one of the plurality of channels 1908 of stent 1902 couples to expandable device 1904 for providing a medium. In at least one exemplary embodiment, expandable device 1904 is a balloon type structure that is expanded with a gas. As expandable device 1904 expands, foam 1906 is stretched to accommodate the increase in volume. In general, foam 1906 is flexible and can stretched to accommodate a range of ear canal sizes. The membrane 1907 would correspondingly expand such that the tensile stress increases thereby changing the reflectivity and frequency response. Expandable device 1904 allows the force to be controlled and varied for pressing the membrane against the ear canal wall. Having control over the force allows similar pressures to be applied whether the ear canal has a small or large diameter. Environmental correction could be applied automatically by sensing sound in the ambient environment. For example, in a low noise environment, a low force could be applied to maintain the acoustic seal between the membrane and ear canal to maximize comfort. Conversely, the force could be increased to further the attenuation of foam device 1900 in a high noise environment to protect the user's ear and create the isolated ear canal volume (from noise in the ambient). The mitigation of the occlusion effect would allow an ear canal microphone to be used to communicate in the high noise environment with little degradation in the voice quality and articulation. In another embodiment, the increased force can be used to ensure a liquid seal is achieved by foam device 1906.

Figure 20:
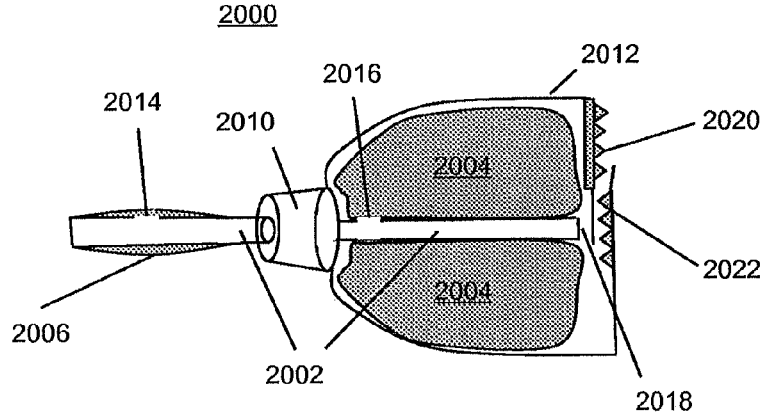
FIG. 20 is a cross-sectional view of an inflation system in a quiescent state in accordance with at least one exemplary embodiment.

FIG. 20 is a cross-sectional view of an inflation system 2000 in a quiescent state in accordance with at least one exemplary embodiment. Inflation system 2000 includes an expandable device 2006 (in a non-expanded state), a variable volume housing 2012, a support structure 2002, and a resilient reservoir 2004. In at least one exemplary embodiment, inflation system 2000 is used to isolate an ear canal volume from an ambient environment. Expandable device 2006 is mounted on support structure 2002 and has a benign profile for inserting into the ear canal. A flange 2010 limits the insertion depth of support structure 2002 to a depth typically less than half the length of an average ear canal. Flange 2010 can also seal the ear canal opening to improve sound isolation. A medium (e.g. gas, liquid, or gel) in an interior volume of resilient reservoir 2004 is transferred to expandable device 2006 after expandable device 2006 is inserted into the ear canal. Expandable device 2006 is then expanded until an acoustical seal is formed with the ear canal wall thereby forming an isolated ear canal volume.

The quiescent state corresponds to the condition where no force is applied to resilient reservoir 2004. Resilient reservoir 2004 resides in variable volume housing 2012 and has a maximum interior volume in the quiescent state. A securing mechanism comprising elements 2020 and 2022 are decoupled from one another such that no force is applied to resilient reservoir 2004. Expandable device 2006 can be a variable volume or fixed volume balloon. The variable volume balloon has little or no interior volume when the resilient reservoir 2004 is in the quiescent state as it returns to a state of least tensile stress. Support structure 2002 includes a channel that couples expandable device 2006 to resilient reservoir 2004. The channel of support structure 2002 has an opening 2014 that couples to the interior volume of expandable device 2006 and an opening 2016 that couples to the interior volume of resilient reservoir 2004.

Figure 21:
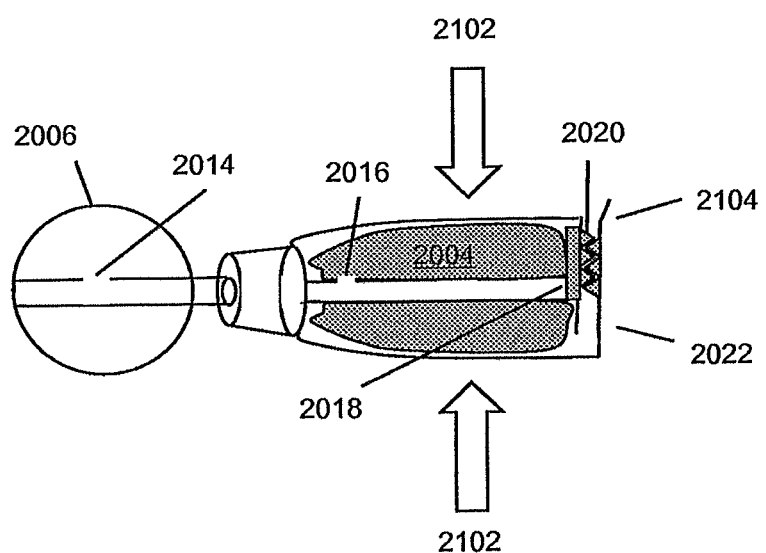
FIG. 21 is a cross-sectional view of the inflation system with an expanding device expanded in accordance with at least one exemplary embodiment.

FIG. 21 is a cross-sectional view of inflation system 2000 with an expanding device expanded in accordance with at least one exemplary embodiment. Expandable device 2006 is inserted in the ear canal in an un-expanded state. Support structure 2002 is formed of a flexible and compliant material and is used to direct expandable device 2006 into the ear canal. In at least one exemplary embodiment, a user holds system 2000 between thumb and forefinger in contact with variable volume housing 2012 as indicated by arrows 2102. Housing 2012 can have finger holds that aid in gripping and locating the appropriate spot for expanding expandable device 2006. Expandable device 2006 is inserted in the un-expanded state until flange 2010 contacts the ear canal opening. In at least one exemplary embodiment, flange 2010 is formed to be compliant (e.g. foam or conformable element) to seal or partially seal the ear canal opening thereby minimizing the sound entering the ear canal from the ambient environment. In a non-limiting example, flange 2010 physically stabilizes system 2000 from movement or torquing once established in the ear canal.

In at least one exemplary embodiment, a force is applied to variable volume housing 2012 that reduces the volume of resilient reservoir 2004. As indicated by arrows 2102, pinching or squeezing variable volume housing 2012 transfers the medium from resilient reservoir 2004 to expandable device 2006. In a non-limiting example, resilient reservoir 2004 is filled with air. As described hereinabove, resilient reservoir 2004 is coupled to expandable device 2006 through support structure 2002. The air is transferred through opening 2016 into the channel in support structure 2002 and out of opening 2014. Squeezing variable volume housing 2012 increases the pressure of the gas in resilient reservoir 2004 until the pressure overcomes the elastic force of the membrane of expandable device 2006. Once the elastic force is overcome, air from resilient reservoir expands expandable device 2006 in the ear canal. In an example where expandable device 2006 is a fixed volume balloon the medium is transferred to the interior volume of the balloon (e.g. no elastic force need be overcome). The interior volume of resilient reservoir 2004 is less when expandable device 2006 is inflated than the volume in the quiescent state. In general, the user expands expandable device 2006 until an acoustic seal is formed between the membrane of expandable device 2006 and the ear canal wall. Expandable device 2006 can expand to acoustically seal a statistically large ear canal. Similarly, resilient reservoir has sufficient interior volume to fill expandable device 2006 for the statistically large ear canal under a variety of operating conditions.

The securing mechanism comprises elements 2020 and 2022 to lock variable volume housing 2012 at a volume selected by the user of system 2000. In at least one exemplary embodiment, elements 2020 and 2022 have opposing teeth that interconnect as the volume of resilient reservoir 2004 is reduced. The pressurized air of resilient reservoir 2004 places an outward force on variable volume housing 2012. The teeth ratchet together (as shown) as resilient reservoir 2004 is squeezed to transfer the volume to expandable device 2006. In at least one exemplary embodiment, the teeth of elements 2020 and 2022 can be sloped to interlock and hold the position. The outward force applied by resilient reservoir 2004 and the teeth slope combine to retain housing 2012 in the fixed position.

Resilient reservoir 2004 can be released to expand back to the quiescent state by separating elements 2020 and 2022 from one another. In at least one exemplary embodiment, a finger can access a tab 2104 of element 2022. Pulling tab 2104 away from element 2020 breaks the interlock between the teeth of elements 2020 and 2022 and returns system 2000 to the quiescent state shown in FIG. 20. Once released, the elastic force of the membrane of expandable device 2006 forces the gas through opening 2014, into the channel of support structure 2002, and exits through opening 2016 into resilient reservoir 2004. System 2000 can be removed from the ear canal when expandable device 2006 is in an unexpanded state.

In general, the membrane of expanding device 2006 will return to an equilibrium state balanced against the conditions of the medium in resilient membrane 2004. For example, expandable device 2006 is a variable volume balloon. The elastic force of the balloon will return to the state of least tensile stress. In at least one exemplary embodiment, resilient reservoir 2004 stores the air at approximately the ambient atmospheric pressure. The variable balloon would return to a state having a minimum interior volume since there would not be sufficient pressure in resilient reservoir 2004 to overcome the elastic force of the membrane. Resilient reservoir 2004 can be molded from resilient material that repeatably returns to a predetermined shape and predetermined volume in the quiescent state. Incremental adjustment can be achieved by maintaining a force on the variable volume housing 2012 while releasing element 2022 from element 2020. The pressure can then be increased or decreased (by adjusting the force) applied to housing 2012 based on the user preference and then fixed by engaging elements 2020 and 2022 together.

The membrane of expandable device 2006 can leak the medium over time. The membrane permeability will determine the leakage rate of the medium. Typically, the membrane is selected such that expandable device 2006 will maintain an acoustic seal for an extended period of time. For example, it is anticipated that system 2000 can be worn for periods such as 4 hours, 8 hours, or 12 hours and maintain the acoustic seal isolating the ear canal volume. Thus, the entire medium does not return to resilient reservoir 2004 after system 2000 has been used for an extended period of time due to leakage.

Figure 22:
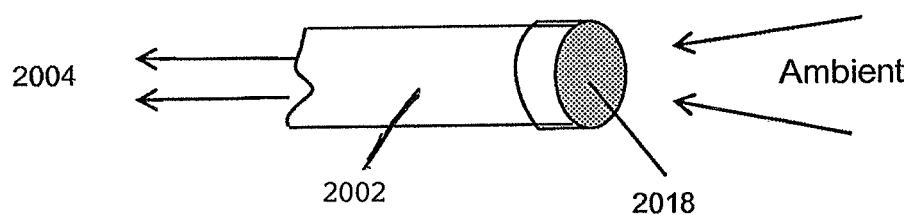
FIG. 22 is an illustration of a support structure having a permeable membrane in accordance with at least one exemplary embodiment.

FIG. 22 is an illustration of support structure 2002 having a permeable membrane in accordance with at least one exemplary embodiment. A distal end of support structure 2002 corresponds to the portion inserted into the ear canal and does not have an opening for an earplug application. A proximal end of support structure 2002 corresponds to a side adjacent to the ambient environment. Membrane 2018 covers an exposed channel opening at the proximal end of support structure 2002. Membrane 2018 is permeable to the medium. For example, membrane 2018 can be a silicone membrane that is permeable to a gas such as air. Referring to FIG. 21, when expandable device 2006 is expanded a cover on element 2020 covers membrane 2018. Element 2020 aligns with and covers membrane 2018 when variable volume housing 2012 is in a reduced volume state (expandable device 2006 is inflated) and elements 2020 and 2022 are interlocked. Covering membrane 2018 when expandable device 2006 is expanded prevents leakage of the medium through membrane 2018. Referring to FIG. 20, elements 2020 and 2022 are disconnected from one another. Membrane 2018 of support structure 2002 is not covered by element 2020. Membrane 2018 is exposed to gas (e.g. air) in the ambient. The gas in the ambient diffuses through membrane 2018 to replenish the gas lost due to leakage while expandable device 2006 was expanded thereby returning resilient reservoir 2004 to the quiescent state. Thus, membrane 2018 fills resilient reservoir 2004 passively by exposure to the ambient when expandable device 2006 is in an unexpanded state.

Figure 23:
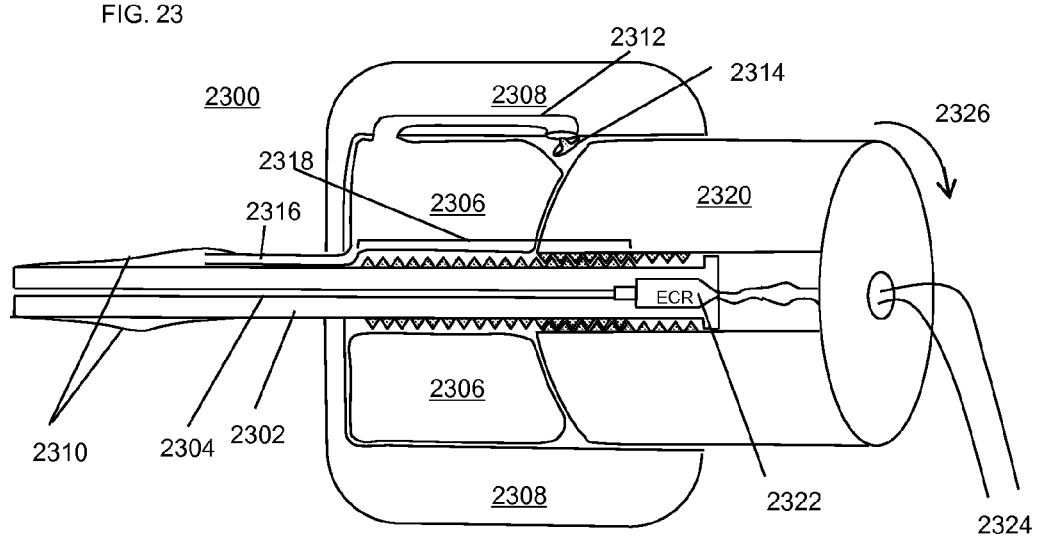
FIG. 23 is a cross-sectional view of an inflation system in a quiescent state in accordance with at least one exemplary embodiment.

FIG. 23 is a cross-sectional view of an inflation system 2300 in a quiescent state in accordance with at least one exemplary embodiment. In at least one exemplary embodiment, system 2300 occludes an ear canal to create an isolated ear canal volume. Inflation system 2300 comprises a support structure 2302, a housing 2308, a resilient reservoir 2306, a threaded device 2320, and an expandable device 2310. Support structure 2302 can include one or more acoustic channels for delivering or receiving sound. In at least one exemplary embodiment, an acoustic channel 2304 in support structure 2302 couples to an ear canal receiver 2322 at a proximal end of structure 2302. Acoustic channel 2304 ends in a port at a distal end of structure 2302 for delivering sound from ear canal receiver 2322 to the isolated ear canal volume.

Housing 2308 couples to support structure 2302. A major surface of housing 2308 is larger than an ear canal opening. The major surface rests against a concha region of the outer ear thereby limiting the insertion depth of support structure 2302 into the ear canal. Housing 2308 can include a foam or flexible insert (not shown) for sealing an ear canal opening as the major surface rests against the concha region. In at least one exemplary embodiment, resilient reservoir 2306 overlies a threaded region 2318 of support structure 2302 and resides within housing 2308. Resilient reservoir 2306 stores sufficient medium for expanding expandable device 2310 to acoustically seal a statistically large ear canal. Housing 2308 includes an opening on the proximal side for receiving threaded device 2320. Threaded device 2320 is threaded onto threaded region 2318. Rotating 2326 threaded device 2320 moves the device into or out of housing 2308.

Expandable device 2310 overlies support structure 2302 at the distal end and is shown in an un-expanded state. Expandable device 2310 comprises a flexible material that can be expanded by a medium such as a gas, liquid, or gel. Resilient reservoir 2306 includes a channel 2316 coupled to an interior volume of expandable device 2310 and a channel 2312. In at least one exemplary embodiment, resilient reservoir 2306 is filled with a gas such as air. The air in reservoir 2306 is used to inflate expandable device 2310. Air that is lost due to leakage from system 2300 is passively replenished through channel 2312. In a non-limiting example, reservoir 2306 is formed from a resilient material such that it returns to predetermined volume corresponding to the quiescent state when threaded device 2320 is not in contact with reservoir 2306. A cover 2314 of channel 2312 is open when expandable device 2310 is in the un-expanded state. The port of channel 2312 is exposed to the ambient environment providing air to fill resilient reservoir to the predetermined volume of the quiescent state.

The interior volume of housing 2308 is reduced as threaded device 2320 displaces the interior space inside of the housing. Threaded device 2320 includes a chamber for receiving support structure 2302 as the interior volume in housing 2308 is reduced. Wires 2324 from ear canal receiver 2322 extend through the chamber and out of threaded device 2320 for coupling to receive a signal. Cover 2314 seals the port of channel 2312 as threaded device 2320 contacts resilient reservoir 2306. The movement of threaded device 2320 closes the cover over the port and then keeps it sealed by being sandwiched between a major surface of threaded device 2320 and the port of channel 2312. Thus, expandable device 2310 and resilient reservoir 2306 form a sealed system once the port of channel 2312 is closed.

Figure 24:
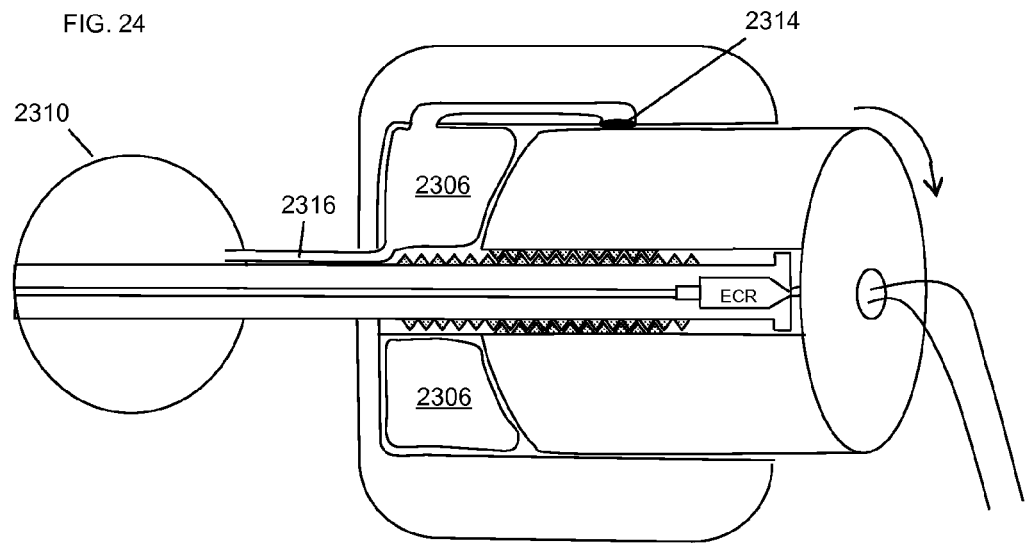
FIG. 24 is a cross-sectional view of an inflation system with an expandable device expanded in accordance with at least one exemplary embodiment.

FIG. 24 is a cross-sectional view of inflation system 2300 with expandable device 2310 expanded in accordance with at least one exemplary embodiment. Rotating threaded device 2320 to move into housing 2308 reduces the volume of resilient reservoir 2306. The displaced medium is transferred from reservoir 2306 through channel 2316 to expandable device 2310. For example, if the medium is air and expandable device 2310 is a variable volume balloon threaded device 2320 will compress the gas in resilient reservoir 2306 (increasing the pressure) until the elastic force of the membrane of the variable volume balloon is overcome. Expandable device 2310 will increase in diameter as more of the volume of reservoir 2306 is reduced by device 2320. Expandable device 2310 is expanded until an acoustic seal is formed between the membrane of the balloon and the ear canal wall thereby forming an isolated ear canal volume. Adjustment of the amount of medium transferred to expandable device 2310 is easily adjusted by rotating device 2320 to increase or decrease the volume of reservoir 2306 thereby modifying the amount of medium in expandable device 2310.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 20 mils) should be interpreted to be "about" the value of the stated number (e.g., about 20 mils).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A system to occlude an ear canal comprising:
an expandable device;
a reservoir for storing a medium;
a channel operatively coupled between the expandable device and the reservoir; and
a pump operatively coupled to the reservoir;
where the pump is configured to expand the expandable device to a predetermined internal pressure and to increase a stress of a surface of the expandable device to a predetermined stress via transfer of the medium from the reservoir to the expandable device, such that at least a majority portion of the surface of the expandable device contacts a bony region or a cartilaginous region of an ear canal wall and imparts a force along a substantial surface of the ear canal wall to a majority of the depth of the bony region or of the cartilaginous region of the ear canal to achieve the predetermined internal pressure and seal against the canal wall to reduce an occlusion effect, and
where the predetermined stress and the predetermined internal pressure are selected according to a predetermined relationship to produce a predetermined attenuation of bodily-propagated sound such that the bodily-propagated sound is attenuated more below a predetermined frequency than above the predetermined frequency, to reduce the occlusion effect by the bodily-propagated sound.

2. The system according to claim 1, where the expandable device includes an expandable bladder configured to receive the medium.

3. The system according to claim 1, where the medium includes at least one of a gas, a liquid or a gel.

4. The system according to claim 3, where the gas includes air.

5. A method of voice pickup comprising:
expanding an expandable device configured to expand in an ear canal of a user, forming a sealed chamber between a distal end of the expandable device and an ear drum of the ear canal, where the expandable device is expanded to a predetermined internal pressure and to increase a stress of a surface of the expandable device to a predetermined stress, such that at least a majority portion of the surface of the expandable device contacts a bony region or a cartilaginous region of an ear canal wall and imparts a force along a substantial surface of the ear canal wall to a majority of a total depth of the bony region or of the cartilaginous region of the ear canal to achieve the predetermined internal pressure and seal against the canal wall to reduce an occlusion effect, where the predetermined stress and the predetermined internal pressure are selected according to a predetermined relationship to produce a predetermined attenuation of bodily-propagated sound such that the bodily-propagated sound is attenuated more below a predetermined frequency than above the predetermined frequency, to reduce the occlusion effect by the bodily-propagated sound; and
picking up a voice of the user with an Ear Canal Microphone (ECM), where the ECM is positioned to sample an acoustic environment of the sealed chamber.

6. The system according to claim 1, where the expandable device includes:
an expandable bladder configured to receive the medium; and
a foam material disposed between the expandable bladder and the ear canal wall.

7. The system according to claim 6, further comprising a membrane disposed on the foam material and configured to contact the ear canal wall.

8. The system according to claim 1, further comprising at least one microphone.

9. The system according to claim 8, where the at least one microphone includes an ambient sound microphone (ASM).

10. The system according to claim 8, where the at least one microphone includes an ear canal microphone (ECM).

11. The system according to claim 10, where a sealed chamber is formed between an ear drum and a distal end of the expandable device, where a reduction of the occlusion effect improves a voice pickup by the ECM.

12. The system according to claim 1, further comprising a stop flange to control an insertion depth of the expandable element in the ear canal.

13. The system according to claim 1, where the force imparted by the surface is selected to attenuate the bodily-propagated sound below the predetermined frequency and to pass the bodily-propagated sound above the predetermined frequency, to reduce the occlusion effect below the predetermined frequency.

14. The system according to claim 13, where the predetermined frequency is about 500 Hz.

15. The system according to claim 1, where the force is due to at least one of a radial force by the surface or a tensile stress of the surface.

16. The method according to claim 5, where a reduction of the occlusion effect improves a quality of the voice that is picked up by the ECM.

17. The method according to claim 5, where the force imparted by the surface is selected to attenuate the bodily-propagated sound below the predetermined frequency and to pass the bodily-propagated sound above the predetermined frequency, to reduce the occlusion effect below the predetermined frequency.

18. The method according to claim 17, where the predetermined frequency is about 500 Hz.

19. The method according to claim 5, where the force is due to at least one of a radial force by the surface or a tensile stress of the surface.

20. The system according to claim 1, where the force on the ear canal wall produces a tensional strain in the ear canal wall forming a strained ear canal wall, the strained ear canal wall impeding the bodily-propagated sound from entering the ear canal through the ear canal wall.

21. The method according to claim 5, where the force on the ear canal wall produces a tensional strain in the ear canal wall forming a strained ear canal wall, the strained ear canal wall impeding the bodily-propagated sound from entering the ear canal through the ear canal wall.

* * * * *